United States Patent

Tsushima

(10) Patent No.: US 12,042,330 B2
(45) Date of Patent: Jul. 23, 2024

(54) ULTRASOUND SIGNAL PROCESSING DEVICE, ULTRASOUND DIAGNOSTIC DEVICE, AND ULTRASOUND SIGNAL PROCESSING METHOD

(71) Applicant: Konica Minolta, Inc., Tokyo (JP)

(72) Inventor: Mineo Tsushima, Souraku Gun Kyoto (JP)

(73) Assignee: KONICA MINOLTA, INC., Tokyo (JP)

( * ) Notice: Subject to any disclaimer, the term of this patent is extended or adjusted under 35 U.S.C. 154(b) by 939 days.

(21) Appl. No.: 16/517,862

(22) Filed: Jul. 22, 2019

(65) Prior Publication Data

US 2020/0077977 A1 Mar. 12, 2020

(30) Foreign Application Priority Data

Sep. 11, 2018 (JP) ................................ 2018-169515

(51) Int. Cl.
*A61B 8/14* (2006.01)
*A61B 8/00* (2006.01)
(Continued)

(52) U.S. Cl.
CPC .............. *A61B 8/14* (2013.01); *A61B 8/4488* (2013.01); *G01N 29/221* (2013.01); *G01N 29/44* (2013.01)

(58) Field of Classification Search
CPC ...... A61B 8/14; A61B 8/4488; G01N 29/221; G01N 29/44; G01N 2291/011;
(Continued)

(56) References Cited

U.S. PATENT DOCUMENTS

2016/0199038 A1* 7/2016 Tsushima ............. A61B 8/4494
600/443
2016/0278742 A1* 9/2016 Tsushima ............... G16H 30/20
2017/0128038 A1* 5/2017 Tsushima ............ G01S 15/8997

FOREIGN PATENT DOCUMENTS

JP S60-129037 A 7/1985

OTHER PUBLICATIONS

M. Itou, et al; Ultrasound Diagnostic Equipment; Corona Publishing Co., Ltd; Aug. 26, 2002; pp. 42-45 (partial translation) (Year: 2002).*

(Continued)

*Primary Examiner* — Patrick Fernandes
*Assistant Examiner* — Nicholas A Robinson
(74) *Attorney, Agent, or Firm* — LUCAS & MERCANTI, LLP

(57) ABSTRACT

An ultrasound signal processing device including a transmitter, a receiver, an observation point setter, and a frame generator. The transmitter repeatedly performs a transmission event, changing a position of a transducer array for each transmission event, the transmission event including selecting the transducer array from transducers on an ultrasound probe and outputting a drive signal driving the transducer array to transmit focused transmitted ultrasound. The receiver receives signals from the ultrasound probe to generate signal sequences, the signals being based on reflected ultrasound acquired by the ultrasound probe. The observation point setter sets observation points corresponding to positions in the subject. The frame generator generates a frame acoustic line signal based on the signal sequences corresponding to each of the observation points. The observation points are set such that observation points in a region shallower than a focal region each correspond to only one transmission event.

12 Claims, 17 Drawing Sheets

(51) Int. Cl.
*G01N 29/22* (2006.01)
*G01N 29/44* (2006.01)

(58) Field of Classification Search
CPC ..... G01N 29/0645; G01N 2291/02475; G01N 2291/106; G01N 29/069; G01N 29/07
See application file for complete search history.

(56) References Cited

OTHER PUBLICATIONS

M. Itou, et al; Ultrasound Diagnostic Equipment; Corona Publishing Co., Ltd; Aug. 26, 2002; pp. 42-45 (partial translation).
S.I. Nikolov, et al; Virtual ultrasound sources in high resolution ultrasound imaging; Proc. SPIE—Progress in biomedical optics and imaging; vol. 3; 2002; pp. 395-405.

* cited by examiner

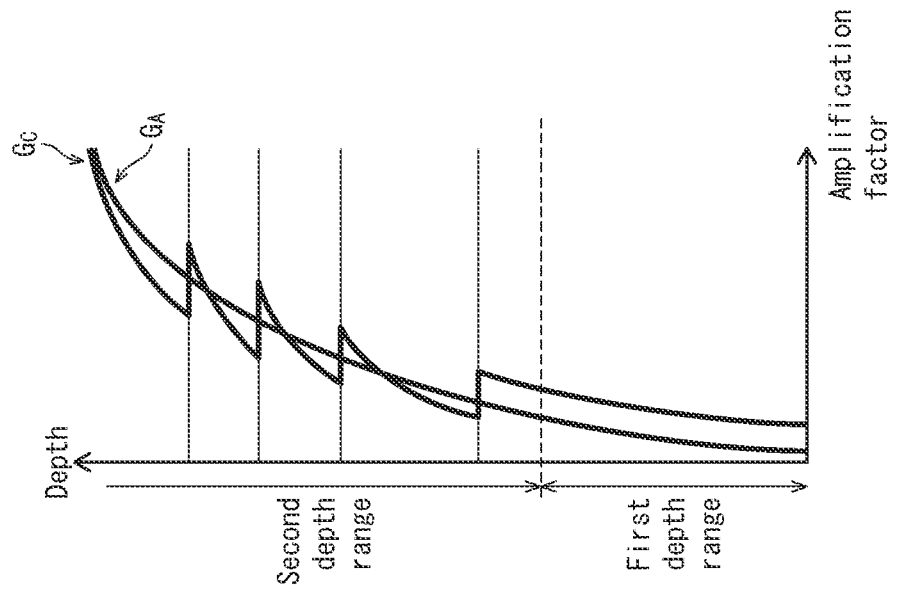
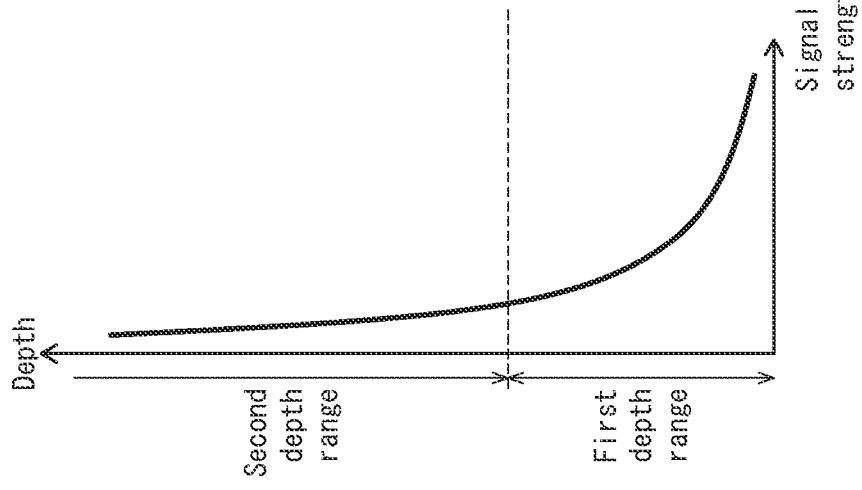
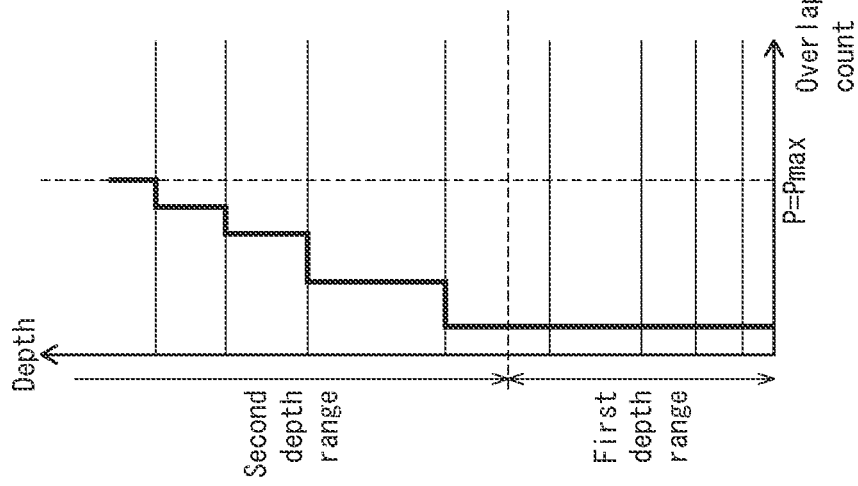

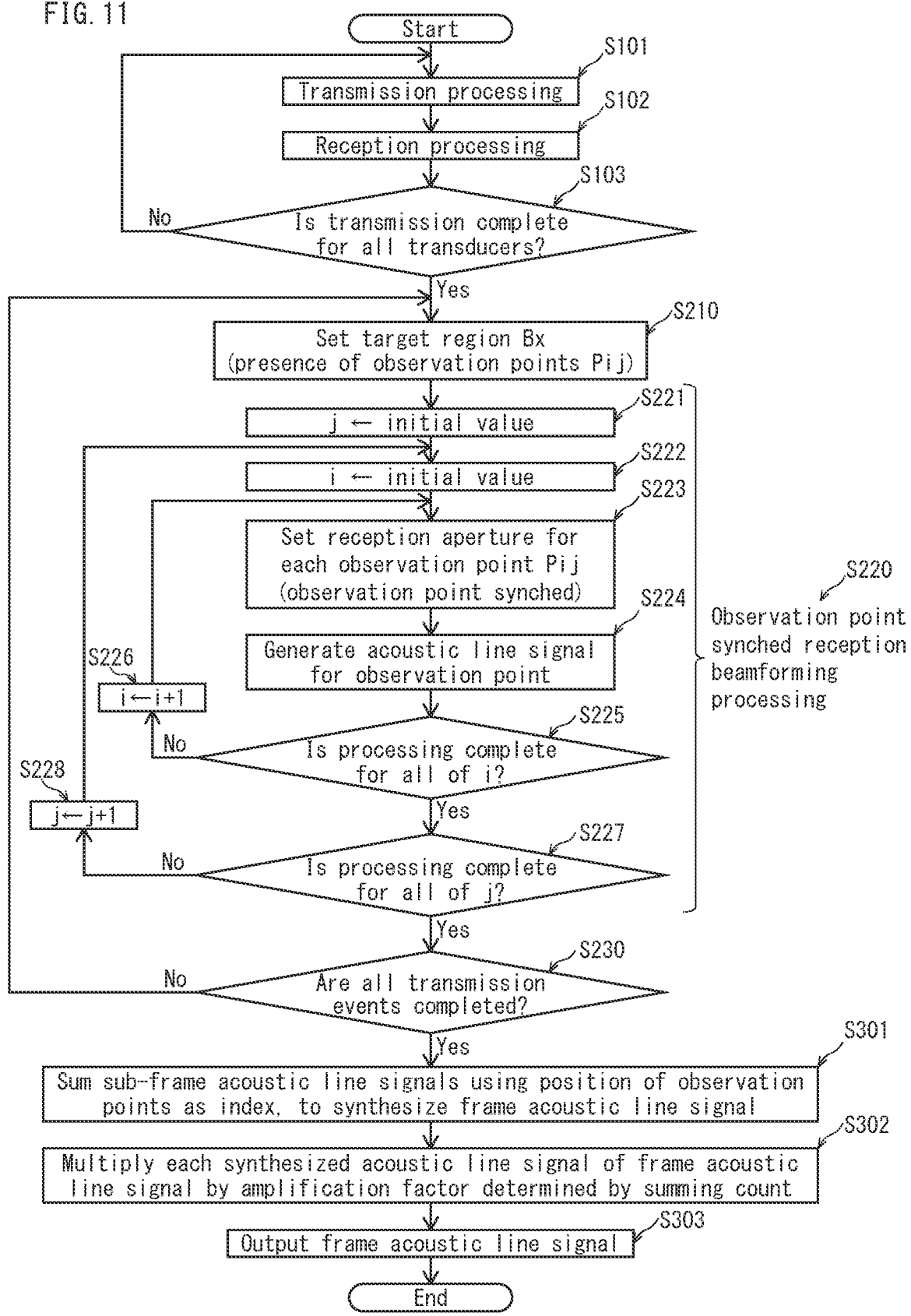

ULTRASOUND SIGNAL PROCESSING DEVICE, ULTRASOUND DIAGNOSTIC DEVICE, AND ULTRASOUND SIGNAL PROCESSING METHOD

This application claims priority to Japanese Patent Application No. 2018-169515 filed Sep. 11, 2018, the contents of which are hereby incorporated herein by reference in their entirety.

BACKGROUND

(1) Technical Field

The present disclosure relates to ultrasound signal processing devices and ultrasound diagnostic devices equipped with the same, and particularly to reception beamforming processing in ultrasound signal processing devices.

(2) Description of the Related Art

An ultrasound diagnostic device transmits ultrasound to the inside of a subject via an ultrasound probe (hereinafter also referred to as a probe), and receives reflected ultrasound (echoes) caused by a difference in acoustic impedance of tissue in the subject. Further, the ultrasound diagnostic device generates an ultrasound tomographic image representing structure of internal tissue of the subject based on electric signals acquired through reception of the reflected ultrasound, and displays the ultrasound tomographic image on a monitor (hereinafter also referred to as a display). Ultrasound diagnostic devices are widely used for morphological diagnoses of living bodies because they are not very invasive and can be used to observe the state of internal tissues in real time via tomographic images and the like.

In conventional ultrasound diagnostic devices, delay-and-sum methods are used as reception beamforming methods based on received reflected waves (for example, see "Ultrasound Diagnostic Equipment", M. Ito and T. Mochizuki, Corona Publishing Co. Ltd, Aug. 26, 2002, pp 42-45). According to this method, typically, when ultrasound transmission is performed by multiple transducers transmitting ultrasound to a subject, transmission beamforming is performed such that an ultrasound beam converges (focuses) at a focal depth inside the subject. Further, according to this method, observation points are set along a central axis of the transmitted ultrasound beam. Thus, one ultrasound transmission event generates only one acoustic line signal along the central axis of the transmitted ultrasound beam or a few acoustic line signals, and therefore ultrasound is not utilized in an efficient manner. Further, there is a technical problem that an acoustic line signal acquired from an observation point distant from the transmission focal point has low spatial resolution and signal-to-noise (S/N) ratio.

In contrast, a synthetic aperture method is a reception beamforming method devised to obtain a high-quality image with high spatial resolution even in regions distant from the transmission focal point (for example, "Virtual ultrasound sources in high resolution ultrasound imaging", S. I. Nikolov and J. A. Jensen, in Proc, SPIE—Progress in biomedical optics and imaging, vol. 3, 2002, pp 395-405). According to this method, delay control is performed taking into consideration both the time for ultrasound to arrive at an observation point and the time for reflected ultrasound to arrive at a transducer from the observation point. Thus, reception beamforming can also make use of reflected ultrasound from areas of the ultrasound primary irradiation region distant from the transmission focal point. Due to this, acoustic line signals can be generated covering the entire ultrasound primary irradiation region from one ultrasound transmission event. Note that in the present disclosure, "ultrasound primary irradiation region" indicates an area such that at every point therein, ultrasound transmitted from transducers composing a transmission transducer array is in-phase. In addition, the synthetic aperture method enables acquiring an ultrasound image with higher spatial resolution and higher S/N ratio through virtual alignment with respect to a transmission focal point based on multiple reception signals acquired for the same observation point over multiple transmission events.

SUMMARY

In the synthetic aperture method, for efficient use of ultrasound and high resolution, it is preferable that a region for which acoustic line signals for a single transmission event are generated (hereinafter also referred to as a target region) should have large size, and it is further preferable that the entire ultrasound primary irradiation region should be used as the target region. However, when the number of observation points and computation load increases, a high-performance computing device and large-capacity memory are required, leading to an increase in cost of ultrasound diagnostic devices. Further, in a shallow region between the transmission focal point and the ultrasound probe, the number of reception signals used for virtual transmission focus increases closer to the ultrasound probe, and therefore dependency of acoustic line signal spatial resolution and S/N ratio (hereinafter also referred to as "acoustic line signal quality") on distance to the ultrasound probe is high. When acoustic line signal quality dependency on distance to the ultrasound probe is too high, uniformity of acoustic line signals decreases, and in particular can result in a poor user impression of acoustic line signal quality in regions far from the ultrasound probe.

Aspects of the present disclosure have been achieved in view of the above problem, and the present disclosure aims to provide an ultrasound signal processing device and an ultrasound signal processing method that improve acoustic line signal quality and decrease calculation load when using the synthetic aperture method, and to provide an ultrasound diagnostic device using the same.

The ultrasound signal processing device pertaining to one aspect of the present disclosure is an ultrasound signal processing device comprising ultrasound signal processing circuitry, the ultrasound signal processing circuitry comprising: a transmitter that repeatedly performs a transmission event, changing a position of a transmission transducer array for each transmission event, the transmission event including selecting the transmission transducer array from transducers arrayed on an ultrasound probe and outputting a drive signal to the ultrasound probe for driving the transmission transducer array such that the transducers thereof transmit focused transmitted ultrasound; a receiver that receives signals from the ultrasound probe to generate reception signal sequences, the signals being based on reflected ultrasound reflected in a subject and acquired by the ultrasound probe for each transmission event; an observation point setter that, for each transmission event, sets observation points corresponding to positions in the subject; and a frame generator that generates a frame acoustic line signal based on the reception signal sequences corresponding to each of the observation points set by the observation point setter, wherein the observation point setter sets the observation points such that observation points in a first region each correspond to only one transmission event and observation points in a second region each correspond to more than one transmission event, where a focal region is where the transmitted ultrasound is most focused, the first region is closer than the focal region to the ultrasound probe, and the second region is farther than the focal region from the ultrasound probe.

The ultrasound signal processing device and the ultrasound diagnostic device using the ultrasound signal processing device pertaining to one aspect of the present disclosure can reduce the computation load and increase uniformity of acoustic line signal quality when using the synthetic aperture method.

BRIEF DESCRIPTION OF THE DRAWINGS

The advantages and features provided by one or more embodiments of the disclosure will become more fully understood from the detailed description given hereinbelow and the appended drawings which are given by way of illustration only, and thus are not intended as a definition of the limits of the invention.

FIG. 10A, 10B, 10C are schematic diagrams pertaining to at least one embodiment, illustrating an overview of overlap counts of synthesized acoustic line signals and amplification by an amplification processor 11402.

FIG. 11 is a flowchart illustrating frame acoustic line signal generation operations of the ultrasound diagnostic device 100 pertaining to at least one embodiment.

DETAILED DESCRIPTION

<<Developments Leading to Embodiments>>

Figure 1:
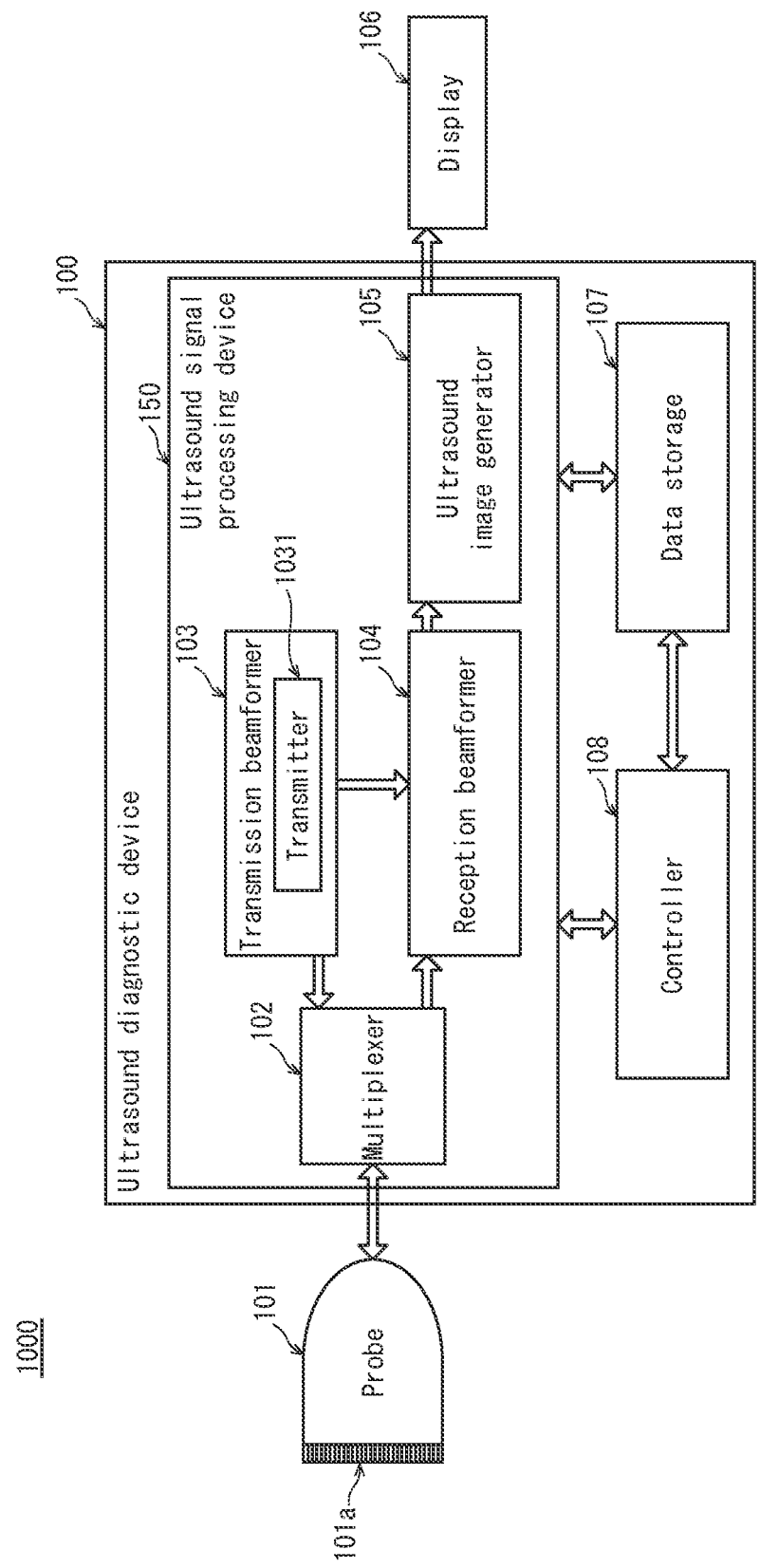
FIG. 1 is a block diagram illustrating structure of an ultrasound diagnostic device 100 pertaining to at least one embodiment.

The inventor conducted various studies to reduce calculation load in ultrasound diagnostic devices using a synthetic aperture method.

According to the synthetic aperture method, first, a target region (a region for which acoustic line signals are generated in one ultrasound transmission event) is set for each transmission event, and reception transducers Rk that receive reflected ultrasound are set for each observation point in the target region. Then, a reception signal is generated for each observation point based on reflected ultrasound received by reception transducers Rk, and delay-and-sum processing of reception signals is performed to generate sub-frame acoustic line signals, thereby generating acoustic line signals corresponding to one transmission event. Then, sub-frame acoustic line signals are synthesized on the basis of positions of observation points, thereby generating a frame acoustic line signal. This achieves virtual transmission focusing.

However, when using a focused ultrasound beam as transmitted ultrasound, the ultrasound primary irradiation region has an hourglass shape where the transmission focal point the narrowest part of the hourglass shape. Accordingly, when the target region is an entire area of the ultrasound primary irradiation region, the farther from the transmission focal point, the greater the number of sub-frame acoustic line signals corresponding to a frame acoustic line signal. Sub-frame acoustic line signal quality tends to decrease farther away from the transmission focal point as transmitted ultrasound focus decreases, and tends to decrease as ultrasound attenuates farther from the ultrasound probe. That is, in a region deeper than the transmission focal point, sub-frame acoustic line signal quality decreases as depth increases, but because the number of sub-frame acoustic line signals corresponding to a frame acoustic line signal increases, sub-frame acoustic line signal quality decrease can be compensated for by a virtual transmission focus, meaning dependency of frame acoustic line signal quality on distance from the ultrasound probe need not be high. On the other hand, in a region shallower than the transmission focal point, the farther an observation point is from the transmission focal point, the closer it is to the ultrasound probe, and the closer an observation point is to the transmission focal point, the farther it is from the ultrasound probe, and therefore sub-frame acoustic line signal quality is not greatly dependent on depth, and in particular, ultrasound attenuation is small and therefore sub-frame acoustic line signal quality is high near the ultrasound probe. Another point is that the farther from the transmission focal point, or in other words the closer to the ultrasound probe, the greater the number of sub-frame acoustic line signals corresponding to a frame acoustic line signal, and therefore frame acoustic line signal quality increases nearer the ultrasound probe. Accordingly, if the target region is an entire area of the ultrasound primary irradiation region, as the region approaches the ultrasound probe, acoustic line signal quality tends to become excessively high. If acoustic line signal quality is excessively high near the ultrasound probe in a B mode image, for example, contrast becomes excessively strong in a shallow region near the ultrasound probe, and as a result quality of a deep region far from the ultrasound probe may be perceived as low, and if adjustments are made aiming to make the deep region as easy to view as the shallow region, the deep region may become unclear or rough.

Thus, in view of the technical problems above, the inventor examined a technique for increasing uniformity of frame acoustic line signal quality in a depth direction and reducing calculation load, and arrived at the ultrasound signal processing device, the ultrasound diagnostic device, and the ultrasound signal processing method pertaining to the following embodiments.

The following embodiments describe the ultrasound signal processing method and the ultrasound diagnostic device including the ultrasound signal processing method in detail, with reference to the accompanying drawings.

<<Embodiments>>

<Overall Structure>

The following is a description of an ultrasound diagnostic device 100 pertaining to at least one embodiment, described with reference to the drawings.

FIG. 1 is a function block diagram of an ultrasound diagnostic system 1000 pertaining to at least one embodiment. As illustrated in FIG. 1, the ultrasound diagnostic system 1000 includes a probe 101, the ultrasound diagnostic device 100, and a display 106. The probe 101 includes transducers 101a. Each of the transducers 101a is capable of transmitting ultrasound towards a subject and receiving reflected ultrasound. The ultrasound diagnostic device 100 causes the probe 101 to perform transmission/reception of ultrasound, and generates an ultrasound image based on signals output from the probe 101. The display 106 displays the ultrasound image on a screen. The probe 101 and the display 106 are each connectable to the ultrasound diagnostic device 100. FIG. 1 illustrates the ultrasound diagnostic device 100 connected to the probe 101 and the display 106. The ultrasound diagnostic device 100 may include therein the probe 101 and the display 106.

<Structure of Ultrasound Diagnostic Device 100>

The ultrasound diagnostic device 100 includes a multiplexer 102, a transmission beamformer 103, and a reception beamformer 104. The multiplexer 102 secures input and output for each transducer used in transmission or reception among the transducers 101a of the probe 101. The transmission beamformer 103 controls timings of application of high voltage to the transducers 101a for ultrasound transmission. The reception beamformer 104 performs amplification and A/D conversion on electric signals obtained by the transducers 101a based on reflected ultrasound received by the probe 101, and performs reception beamforming to generate acoustic line signals. Further, the ultrasound diagnostic device 100 includes an ultrasound image generator 105, a data storage 107, and a controller 108. The ultrasound image generator 105 generates an ultrasound image (a B-mode image) based on signals output from the reception beamformer 104. The data storage 107 stores the acoustic line signal output from the reception beamformer 104 and the ultrasound image output from the ultrasound image generator 105. The controller 108 controls each of the components of the ultrasound diagnostic device 100.

Of these, the multiplexer 102, the transmission beamformer 103, the reception beamformer 104, and the ultrasound image generator 105 are included in ultrasound signal processing circuitry 150. The ultrasound signal processing circuitry 150 constitutes an ultrasound signal processing device.

The components of the ultrasound diagnostic device 100, for example, the multiplexer 102, the transmission beamformer 103, the reception beamformer 104, the ultrasound image generator 105, and the controller 108 each may be implemented by a hardware circuit such as a field-programmable gate array (FPGA) or an application-specific integrated circuit (ASIC). Alternatively, the components each may be implemented by using a combination of software and a programmable device such as a processor. As a processor, a central processing unit (CPU) or a graphics processing unit (GPU) may be used for example, and a structure using a GPU is referred to as a general-purpose graphics processing unit (GPGPU). Each of such components may be implemented as one circuit component or an assembly of circuit components. Further, a plurality of such components may be implemented as one circuit component, or as an aggregate of a plurality of circuit components.

The data storage 107 is a computer-readable recording medium. For example, the data storage 107 may be implemented by using a flexible disk, a hard disk, a magneto-optical (MO) drive, a digital optical disc (DVD, DVD-RAM, BD), or a semiconductor memory. Further, the data storage 107 may be an external storage device connected to the ultrasound diagnostic device 100.

The ultrasound diagnostic device 100 pertaining to the present embodiment is not limited to the ultrasound diagnostic device structure illustrated in FIG. 1. For example, the ultrasound diagnostic device 100 need not include the multiplexer 102, and the transmission beamformer 103 and the reception beamformer 104 may be directly connected to the transducers 101a of the probe 101. Further, the transmission beamformer 130, the reception beamformer 140, or a portion thereof may be inside the probe 110. Such modifications apply not only to the ultrasound diagnostic device 100 pertaining to the present embodiment, but also to other embodiments and modifications of the ultrasound diagnostic device described later in the present disclosure.

<Structure of Components of Ultrasound Diagnostic Device 100>

The ultrasound diagnostic device 100 pertaining to the present embodiment is characterized by the transmission beamformer 103 that causes ultrasound beam transmission from the transducers 101a of the probe 101 and the reception beamformer 104 that receives electric signals from the probe 101 obtained from reception of reflected ultrasound by the probe 101, calculates electric signals, and generates acoustic line signals for generation of an ultrasound image. Accordingly, the present disclosure focuses on the structure and the functions of the transmission beamformer 103 and the reception beamformer 104. Note that components other than the transmission beamformer 103 and the reception beamformer 104 may have structures similar to those in conventional ultrasound diagnostic devices. In other words, the ultrasound diagnostic device 100 may be implemented by replacing beamformers in a conventional ultrasound diagnostic device with the transmission beamformer 103 and the reception beamformer 104 pertaining to the present embodiment.

The following describes the structure of the transmission beamformer 103 and the reception beamformer 104.

1. Transmission Beamformer 103

The transmission beamformer 103 is connected to the probe 101 via the multiplexer 102 and controls timing of high voltage application to each of a plurality of transducers included in a transmission aperture Tx consisting of a transmission transducer array of all or a plurality of the transducers 101a of the probe 101 for transmitting ultrasound from the probe 101. The transmission beamformer 103 includes a transmitter 1031.

Based on a transmission control signal from the controller 108, the transmitter 1031 performs transmission processing to supply a pulsed transmission signal for causing transducers included in the transmission aperture Tx among the transducers 101a of the probe 101 to transmit an ultrasound beam. More specifically, the transmitter 1031 includes, for example, a clock generator circuit, a pulse generator circuit, and a delay circuit. The clock generator circuit is a circuit that generates a clock signal for determining transmission timing of an ultrasound beam. The pulse generator circuit is a circuit for generating a pulse signal that drives a transducer. The delay circuit is a circuit for setting a delay time for each transducer for ultrasound beam transmission timing, delaying ultrasound beam transmission by the delay time in order to perform ultrasound beam focus operations.

The transmitter 1031 repeats ultrasound transmission while gradually shifting the transmission aperture Tx in an array direction by a movement pitch Mp for each ultrasound transmission. According to the present embodiment, the movement pitch Mp is equivalent to one transducer, and therefore the transmission aperture Tx shifts by one transducer in the array direction each ultrasound transmission. The movement pitch Mp is not limited to being equivalent to one transducer, and may be equivalent to half a transducer, for example. Information indicating position of transducers included in the transmission aperture Tx is outputted to the data storage 107 via the controller 108. For example, when a total number of the transducers 101a of the probe 101 is 192, a number of transducers in the transmission aperture Tx may be selected from 20 to 100, for example, and shifted by one transducer per ultrasound transmission. Hereinafter, ultrasound transmission performed from the same transmission aperture Tx by the transmitter 1031 is also referred to as a "transmission event".

Figure 2:
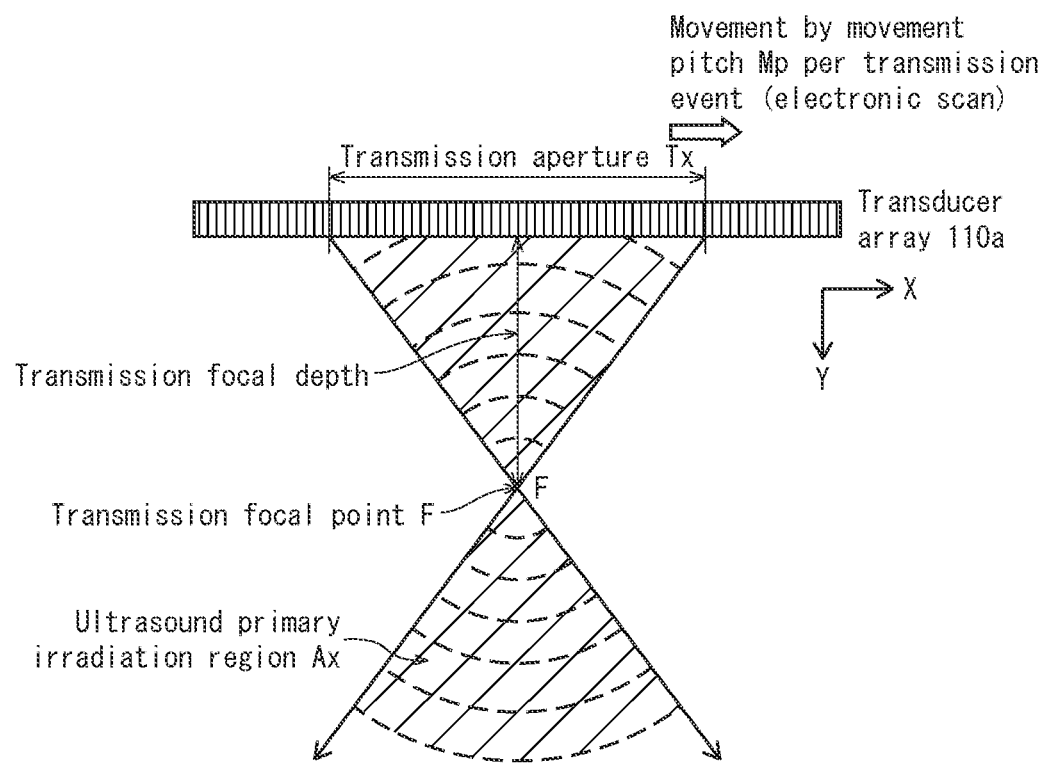
FIG. 2 is a diagram illustrating a propagation path of an ultrasound beam transmitted from a transmission beam former 103 pertaining to at least one embodiment.

FIG. 2 is a schematic diagram illustrating a propagation path of an ultrasound transmission according to the transmission beamformer 103. FIG. 2 illustrates a transmission aperture Tx (i.e., a transmission transducer array of transducers 101a that contribute to ultrasound transmission) in one transmission event. Array length of the transmission aperture Tx may be referred to as transmission aperture length.

In the transmission beamformer 130, transmission timing of each transducer is controlled so that the more central a transducer is in the transmission aperture Tx, the more transmission timing is delayed. As a result, a wavefront of an ultrasound transmission wave transmitted from the transducer array in the transmission aperture Tx converges to a transmission focal point F at a focal depth. Here, the focal depth indicates a depth at which transmitted ultrasound is most focused in the direction along which the transducers are arrayed (X direction in FIG. 2) or in other words, a depth at which the width of ultrasound beams in the X direction is the narrowest. Further, at the focal depth, a position at which energy of ultrasound transmission is highest is referred to as a transmission focal point F, and typically a central position in the X direction of an ultrasound beam at the focal depth is the transmission focal point F. Note that the focal depth is constant for transmission events pertaining to a single frame. In other words, no change occurs in a relative relationship between the transmission aperture Tx and the focal point F for transmission events of a single frame. A wavefront converging at the transmission focal point F diffuses again and the ultrasound transmission propagates in an hourglass-shaped space delimited by two straight lines intersecting at the transmission focal point F with the transmission aperture Tx as the base. That is, an ultrasound wave transmitted from the transmission aperture Tx propagates such that it gradually reduces in width in space (X axis in the drawings) to a minimum width at the transmission focal point F, then as it progresses deeper (Y axis in the drawings), it diffuses as the width increases. In the following, the hourglass-shaped area described above is referred to as an ultrasound primary irradiation region Ax.

However, shape of the ultrasound primary irradiation region Ax is not limited to the hourglass shape intersecting at the focal point F. For example, if the transmission aperture Tx is made small, it is known that convergence at the transmission focal point F does not become narrow, and may result in, for example, a transmission wave that does not converge at one point and diffuse from the focal depth. Further, by setting a delay difference between transducers of the transmission aperture Tx so as to not focus at the transmission focal point F, a defined width in the probe array direction of transmitted ultrasound can be intentionally achieved even at the focal depth. In particular, such transmissions are often used as means to improve frame rates of ultrasound images. Such transmissions are referred to by various names, and methods of forming transmission waves also vary, but transmission having a certain width in the probe array direction even at the focal depth is referred to as broad transmission. Even when broad transmission is used, the ultrasound signal processing device and ultrasound signal processing method of the present disclosure exhibit the effects described later in this disclosure, and therefore transmission including broad transmission is included in the scope of the present disclosure. That is, the transmission focal point F or focal region indicate a region in a subject set to have a high spatial density of ultrasound, and when using broad transmission, a region in the subject through which transmitted ultrasound is intended to propagate is the ultrasound primary irradiation region Ax.

2. Reception Beamformer 104

Figure 3:
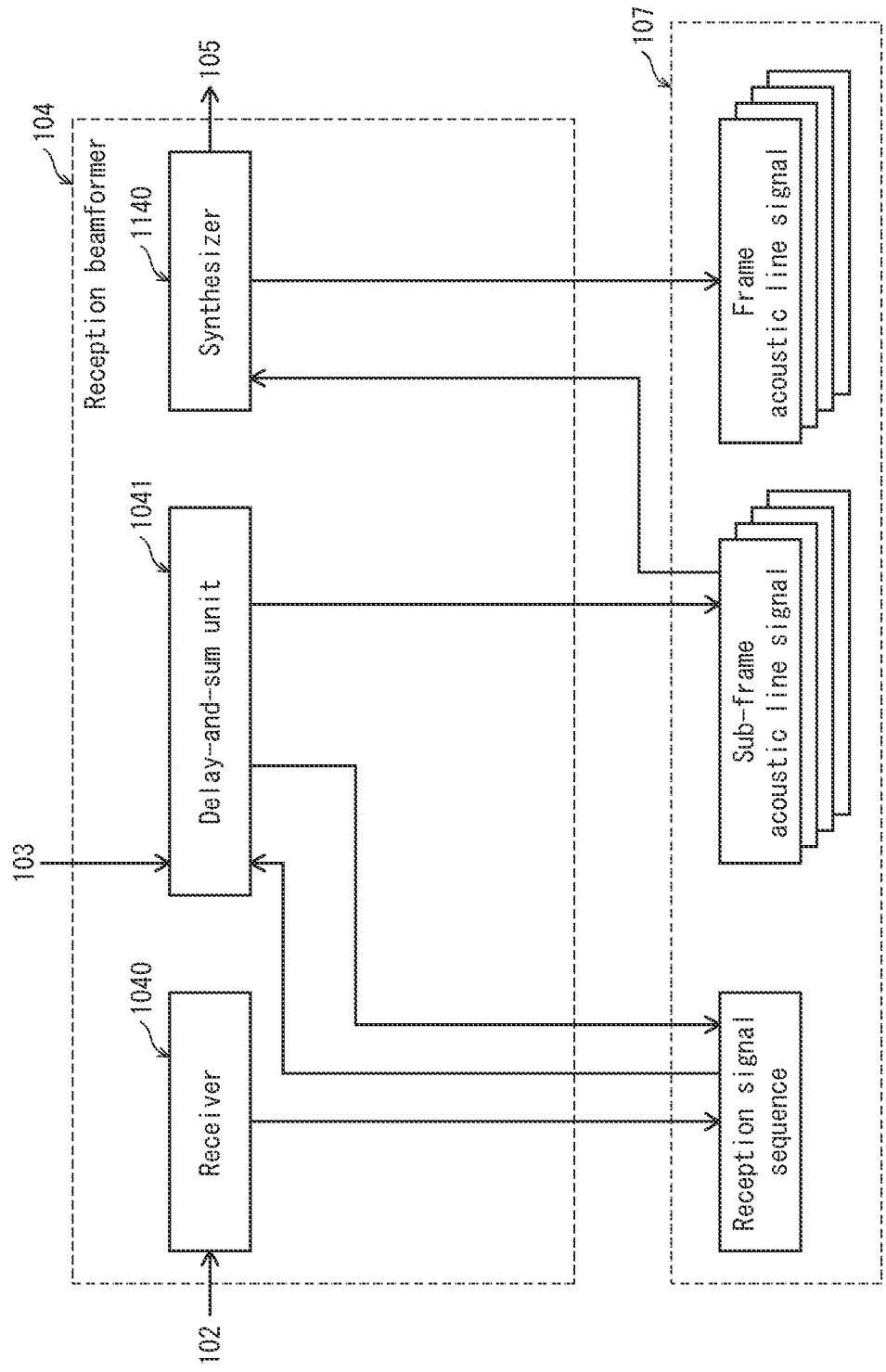
FIG. 3 is a function block diagram illustrating structure of a reception beamformer 104 pertaining to at least one embodiment.

The reception beamformer 104 generates an acoustic line signal from electrical signals obtained by a plurality of the transducers 101a based on reflected ultrasound received by the probe 101. Here, an "acoustic line signal" is a signal after delay-and-sum processing with respect to a given observation point. Delay-and-sum processing is described in more detail later in the present disclosure. FIG. 3 is a function block diagram illustrating structure of the reception beamformer 104. As illustrated in FIG. 3, the reception beamformer 104 includes a receiver 1040, a delay-and-sum unit 1041, and a synthesizer 1140.

The following describes structure of each element of the reception beamformer 104.

(1) Receiver 1040

The receiver 1040 is a circuit that is connected to the probe 101 via the multiplexer 102. For each transmission event, the receiver 1040 generates reception signals (RF signals). The receiver 1040 generates the reception signals by first receiving electric signals acquired through the probe 101 receiving reflected ultrasound, amplifying the received electric signals, and then performing A/D conversion on the amplified signals. The receiver 1040 generates and outputs reception signals in a time sequence in a transmission event order to be stored in the data storage 107.

Here, a reception signal (RF signal) is a digital signal obtained through amplification and AD conversion of an electrical signal converted from reflected ultrasound received by a transducer, and forms a signal sequence in a direction of transmission (depth direction of subject) of ultrasound received by the transducer.

In a transmission event, as stated above, the transmitter 1031 causes each transducer included in the transmission aperture Tx among the transducers 101*a* of the probe 101 to transmit an ultrasound beam. For each transmission event, the receiver 1040 receives electric signals converted in the probe 101 from reflected ultrasound acquired by each of some or all of the transducers 101*a* of the probe 101, thereby to generate a reception signal sequence for each of the transducers 101*a* based on the received electric signals. In the present disclosure, transducers acquiring ultrasound reflected from one or more observation points in one transmission event are referred to as reception transducers. Reception transducers Rk corresponding to each observation point are some or all of the reception transducers. It is beneficial that the number of the reception transducers be greater than the number of transducers included in the transmission aperture Tx.

The receiver 1040 generates a reception signal sequence for each reception transducer in correspondence with a transmission event, and generated reception signal sequences are stored by the data storage 107.

(2) Delay-and-Sum Unit 1041

Figure 4:
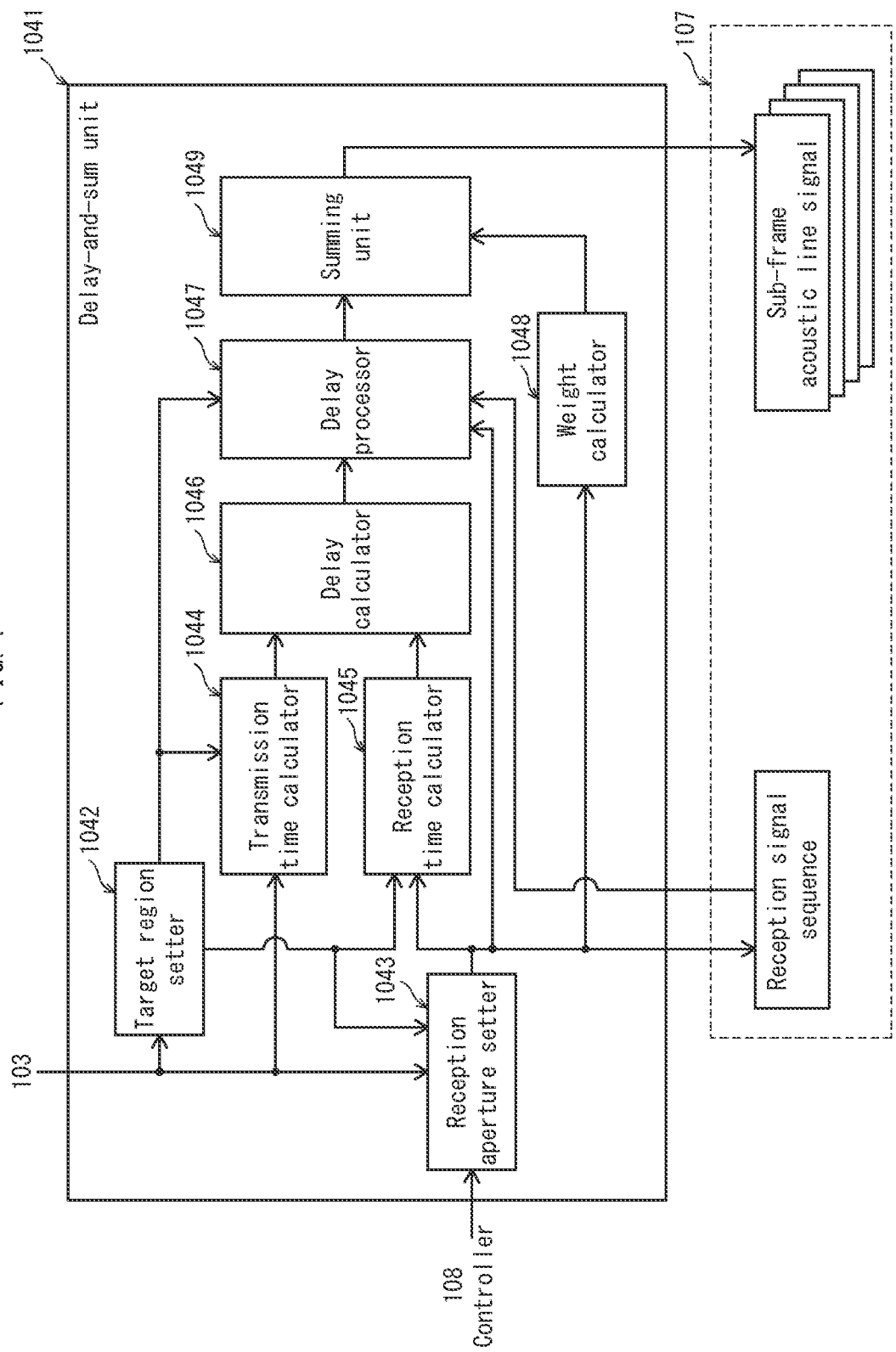
FIG. 4 is a function block diagram illustrating structure of a delay-and-sum unit 1041 pertaining to at least one embodiment.

The delay-and-sum unit 1041 is a circuit that sets a target region Bx for each transmission event. A target region Bx is an area in the subject from which a sub-frame acoustic line signal is to be generated. Further, the delay-and-sum unit 1041 performs, for each observation point Pij of the target region Bx, delay-and-sum processing with respect to reception signal sequences corresponding to the observation point Pij and received by a reception transducer Rk. The delay-and-sum calculator 1041 calculates an acoustic line signal for each of the observation points, thereby to generate a sub-frame acoustic line signal. FIG. 4 is a function block diagram illustrating the structure of the delay-and-sum unit 1041. As illustrated in FIG. 4, the delay-and-sum unit 1041 includes a target region setter 1042, a reception aperture setter 1043, a transmission time calculator 1044, a reception time calculator 1045, a delay calculator 1046, a delay processor 1047, a weight calculator 1048, and a sum calculator 1049.

The following describes the structure of each element of the delay-and-sum unit 1041.

i) Target Region Setter 1042

The target region setter 1042 sets the target region Bx, which is an area in the subject from which a sub-frame acoustic line signal is to be generated. In the present disclosure, the term "target region" is used to indicate a signal area in the subject for generating a sub-frame acoustic line signal for one transmission event. Acoustic line signals are generated for each observation point Pij in the target region Bx. The target region Bx is set as a set of target observation points for which acoustic line signal generation is performed, for the purpose of calculation corresponding to one transmission event.

In the present disclosure, a sub-frame acoustic line signal is a set of acoustic line signals that are generated from one transmission event with respect to all observation points Pij included in the target region Bx. Further, "sub-frame" indicates a unit of a set of signals acquired in one transmission event and corresponding to all the observation points Pij of the target region Bx. Thus, synthesizing multiple sub-frames acquired in different transmission events results in one frame.

The target region setter 1042 sets the target region Bx corresponding to a transmission event, based on information indicating position of the transmission aperture Tx acquired from the transmission beamformer 103.

Figure 5:
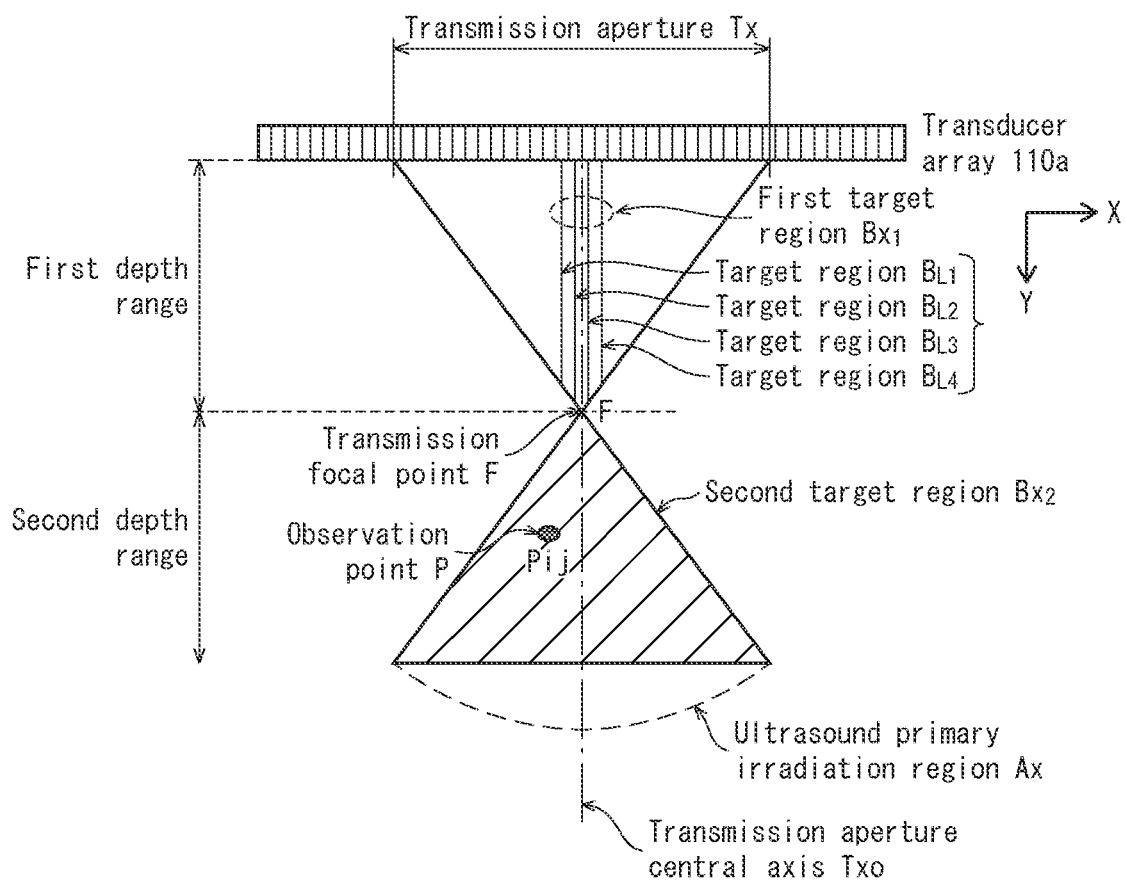
FIG. 5 is a diagram illustrating a target region Bx pertaining to at least one embodiment.

FIG. 5 is a schematic diagram illustrating one example of the target region Bx. As illustrated in FIG. 5, the target region Bx is in the ultrasound primary irradiation region Ax and includes a first target region Bx1 in a first depth range and a second target region Bx2 in a second depth range. The first depth range is a range of depth to a focal depth and the second depth range is a range of depth deeper than the focal depth. The second target region Bx2 is the entirety of the ultrasound primary irradiation region Ax in the second depth range. In contrast, the first target region Bx1 is set as a substantially rectangular area in the vicinity of a central axis of transmitted ultrasound, extending in a direction along the central axis of the transmitted ultrasound. More specifically, the first target region Bx1 is set as a region defined by a plurality of target lines BL1, BL2, BL3, BL4 parallel to a transmission aperture central axis Txo, which is a straight line connecting a center of the transmission aperture Tx to the transmission focal point F. The target lines BL1, BL2, BL3, BL4 are arranged at equal intervals in the array direction (X direction). Further, a width in the array direction of the first target region Bx1 is equal to or less than the movement pitch Mp. That is, the first target regions Bx1 in two consecutive transmission events do not overlap. In other words, observation points Pij in the first target region Bx1 of one transmission event are not set as observation points Pij in other transmission events. Thus, in the first depth range, synthesis of acoustic line signals with respect to the same observation point is not performed, and therefore an excessive difference in spatial resolution and S/N ratio between the first depth range and the second depth range can be prevented. On the other hand, in the second depth range, observation points are set in substantially the entirety of the ultrasound primary irradiation region Ax to improve use efficiency of emitted ultrasound, making it possible to improve spatial resolution and S/N ratio by virtual transmission focusing. Further, an interval between the target line BL4 of one transmission event and the target line BL1 of the next transmission event is beneficially the same as an interval between the target line BL1 and the target line BL2 of the one transmission event. Thus, in subsequent frame acoustic line signals, resolution in the array direction (X direction) can be made uniform. The number of target lines BL included in the first target region Bx1 is not limited to four, and may be any number equal to or greater than one. When the number of the target lines BL included in the first target region Bx1 is an odd number, one of the target lines BL is beneficially on the transmission aperture central line Txo.

The target region Bx set is output to the reception aperture setter 1043, the transmission time calculator 1044, the reception time calculator 1045, and the delay processor 1047.

ii) Reception Aperture Setter 1043

The reception aperture setter 1043 is a circuit that sets a reception aperture Rx based on a control signal from the control unit 108 and information from the target region setter 1042 indicating the target region Bx. The reception aperture setter 1043 selects some of the transducers 101a of the probe 101 as a reception transducer array whose center position corresponds to a transducer spatially closest to an observation point. In a reception transducer array, a transducer included in the reception aperture Rx set per observation point is a reception transducer Rk corresponding to the observation point.

Figure 6:
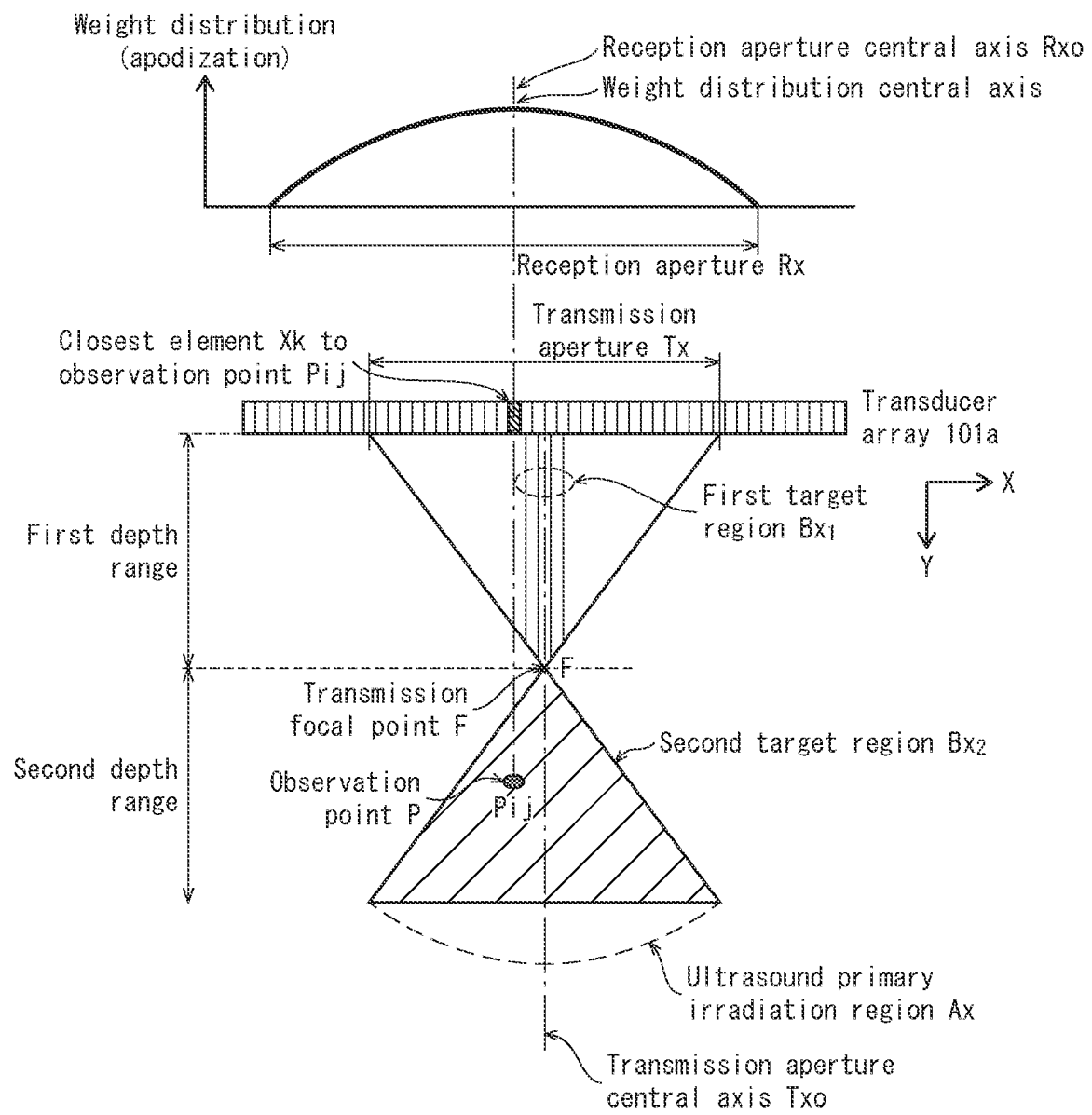
FIG. 6 is a schematic diagram illustrating a relationship between a transmission aperture Tx and a reception aperture Rx set by a reception aperture setter 1043 pertaining to at least one embodiment.

The reception aperture setter 1043 selects the reception aperture Rx such that an array center thereof coincides with a transducer Xk that is spatially closest to an observation point Pij. FIG. 6 is a schematic diagram illustrating the relationship between a transmission aperture Tx and a reception aperture Rx set by the reception aperture setter 1043. As illustrated in FIG. 6, the reception aperture Rx is selected such that the array center of the reception aperture Rx transducer array coincides with the transducer Xk that is spatially closest to the observation point Pij. That is, the reception aperture Rx is selected such that the observation point Pij is on a reception aperture central axis Rxo. Due to this, position of the reception aperture Rx depends upon position of the observation point Pij, and does not change depending upon the position of the transmission aperture Tx, which changes with each transmission event. That is, even in different transmission events, when generating acoustic line signals for a given observation point Pij in the same position, delay-and-sum is performed based on reception signals obtained by the same reception transducers Rk in the same reception aperture Rx.

The configuration of the reception aperture setter 1043 is not limited to the above. For example, a reception aperture may be set such that the transmission focal point F is on the reception aperture central axis Rxo. Further, a method of setting the reception aperture may be different between the first target region Bx1 and the second target region Bx2. For example, with respect to an observation point Pij in the first target region Bx1, the reception aperture may be set such that the transmission focal point F is on the reception aperture central axis Rxo, and with respect to an observation point Pij in the second target region Bx2, the reception aperture may be set such that the observation point Pij is on the reception aperture central axis Rxo. Further, a number of transducers included in the reception aperture Rx for receiving reflected ultrasound from the ultrasound primary irradiation region is beneficially set to be at least the number of transducers included in the transmission aperture Tx of the corresponding transmission event. The number of transducers in the reception aperture Rx may be for example 32, 64, 96, 128, or 192.

Setting of the reception aperture Rx is performed at least a number of times equal to a maximum number of observation points Pij in the array direction. Further, the setting of the reception aperture Rx may be performed each time a transmission event is performed as described above, or alternatively, after multiple transmission events are complete, reception apertures Rx for the multiple transmission events may be set at once.

Information indicating position of transducers included in the reception aperture Rx is outputted to the data storage 107 via the controller 108.

The data storage 107 outputs the information indicating the positions of the reception aperture Rx and reception signals corresponding to reception transducers to the transmission time calculator 1044, the reception time calculator 1045, the delay processor 1047, and the weight calculator 1048.

iii) Transmission time calculator 1044

The transmission time calculator 1044 is a circuit that calculates time required for transmitted ultrasound to arrive at the observation point P in the subject. The transmission time calculator 1044 acquires information indicating the positions of the transducers included in the transmission aperture Tx for a given transmission event from the data storage 107, and information indicating the position of the target region Bx for the transmission event from the target region setter 1042. Based on the information, the transmission time calculator 1044 calculates, for each observation point Pij in the target region Bx, the transmission time required for transmitted ultrasound to arrive at the observation point Pij in the subject.

Figure 7A:
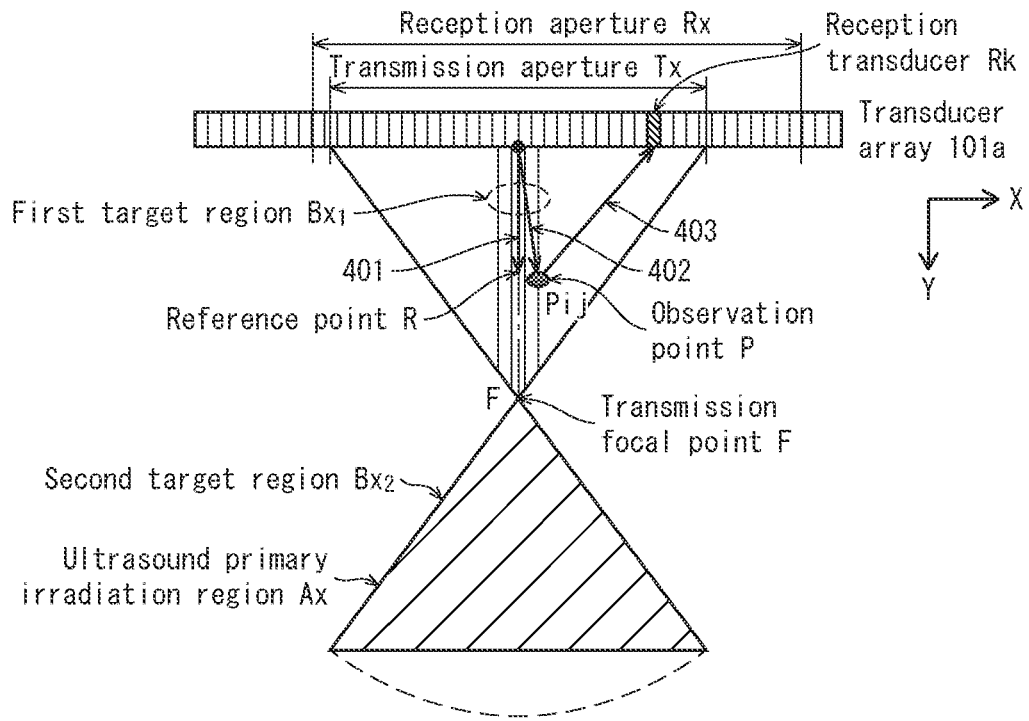
FIG. 7A and FIG. 7B are schematic diagrams pertaining to at least one embodiment, each illustrating a propagation path of ultrasound transmitted from a transmission aperture Tx and arriving at a reception transducer Rk via an observation point Pij.
Figure 7B:
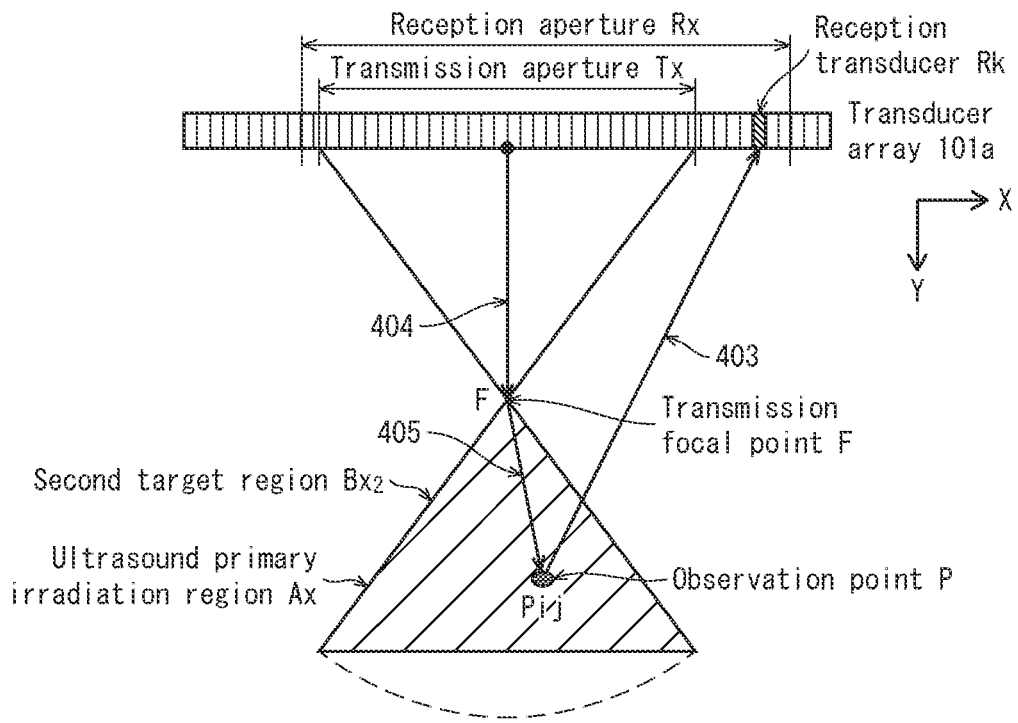

FIG. 7A and FIG. 7B are schematic diagrams each illustrating a propagation path of ultrasound that is transmitted from the transmission aperture Tx, reflected at an observation point Pij in the target region Bx, and arrives at a reception transducer Rk of the reception aperture Rx. FIG. 7A illustrates an observation point Pij located at or shallower than the focal depth. FIG. 7B illustrates an observation point Pij located deeper than the focal depth.

The following describes a case in which the observation point Pij is located deeper than the transmission focal depth, with reference to FIG. 7B. A transmitted wave emitted from the transmission aperture Tx has a wavefront that propagates along a path 404 and converges at a transmission focal point F, then diffuses again. That is, the transmitted wave arrives at an observation point Pij while diffusing, and if there is a change in acoustic impedance at the observation point Pij a reflected wave is generated, the reflected wave returning to a reception transducer Rk in the reception aperture Rx of the probe 110. The transmission focal point F is stored in the device as a design value of the transmission beamformer 103, and therefore the length of a path 405 from the transmission focal point F to the observation point Pij can be calculated geometrically.

The following describes how the transmission time is calculated in further detail. Calculation assumes that ultrasound transmitted from the transmission aperture Tx arrives at the transmission focal point F by travelling along the path 404 and then travels along the path 405 to arrive at the observation point Pij from the transmission focal point F. Accordingly, a value obtained by summing a travel time along the path 404 and a travel time along the path 405 is used as the transmission time of a transmission wave. More specifically, the transmission time can be calculated, for example, by dividing the total of the lengths of paths 404 and 405 by the velocity at which ultrasound propagates within the subject.

On the other hand, the following describes a case in which the observation point Pij is located at or shallower than the focal depth, with reference to FIG. 7A. As described above, observation points Pij in the first target region Bx1 are on or close to the transmission aperture central axis Txo. Accordingly, it can be considered that a transmission wave emitted from a center of the transmission aperture Tx arrives directly at the observation point Pij. Thus, time required to travel along a path 402 from a center of the transmission aperture Tx to the observation point Pij is considered to be the travel time to the observation point Pij. The observation point Pij is on or near the transmission aperture central axis Txo, and therefore transmission time of transmitted ultrasound to the observation point Pij may be considered to be a travel time along a path 401 from the center of the transmission aperture Tx to a reference point R on the transmission aperture central axis Txo at the same Y coordinate as the observation point Pij. As examples of specific calculation methods, length of the path 401 can be divided by the velocity at which ultrasound propagates in the subject, or length of the path 402 can be divided by the velocity at which ultrasound propagates in the subject.

Transmission time when the observation point Pij coincides with the transmission focal point F may use either calculation method described above, as length of the path 405 is zero and the paths 401, 402, 404 are identical.

The transmission time calculator 1044 calculates the transmission times for ultrasound to arrive at each observation point Pij in the target region Bx in a subject for one transmission event, and outputs to the delay calculator 1046.

iv) Reception Time Calculator 1045

The reception time calculator 1045 is a circuit that calculates a reception time required for reflected ultrasound from the observation point P to arrive at each reception transducer Rk of the reception aperture Rx. For a given transmission event, the reception time calculator 1045 acquires information indicating the positions of the reception transducers Rk from the data storage 107, and acquires the information indicating the position of the target region Bx from the target region setter 1042. Based on the information, the reception time calculator 1045 calculates, for each observation point Pij of the target region Bx, the reception time required for transmitted ultrasound to arrive at each reception transducer Rk after being reflected at the observation point Pij in the subject.

As described above, transmitted ultrasound arriving at an observation point Pij generates reflected ultrasound when there is a change in acoustic impedance at the observation point Pij. The reflected ultrasound is then received by reception transducers Rk of the reception aperture Rx. The reception time calculator 1045 acquires position information of the reception transducers Rk of the reception aperture Rx from the data storage 107 and therefore the reception time calculator 1045 is able to geometrically calculate the length of the paths 403 from the observation point Pij to the reception transducers Rk.

For each transmission event, the reception time calculator 1045 calculates, for each observation point Pij in the target region Bx, the time required for transmitted ultrasound to arrive at each reception transducer Rk after reflection at the observation point Pij, and outputs to the delay calculator 1046.

v) Delay Calculator 1046

The delay calculator 1046 is a circuit that calculates, for each reception transducer Rk, a total propagation time based on the transmission time and the reception time for the reception transducer Rk, and further calculates, for each reception transducer Rk, a delay based on the total propagation time to apply to a reception signal sequence for the reception transducer Rk. The delay calculator 1046 acquires, from the transmission time calculator 1044, the transmission time required for ultrasound waves to arrive at an observation point Pij. Further, for each reception transducer Rk, the delay calculator 1046 acquires, from the reception time calculator 1045, the reception time required for ultrasound reflected at the observation point Pij to arrive at the reception transducer Rk. Then, the delay calculator 1046, for each reception transducer Rk, calculates a total propagation time required for transmitted ultrasound to arrive at the observation point Pij, be reflected at the observation point Pij, and then arrive at the reception transducer Rk. Further, based on the differences between total propagation times for the reception transducers Rk, the delay calculator 1046 calculates a delay for each reception transducer Rk. For each observation point P of the target region Bx, the delay calculator 1046 calculates, for each reception transducer Rk, the delay to be applied to a reception signal sequence for the reception transducer Rk, and outputs the delay to the delay processor 1047.

vi) Delay Processor 1047

The delay processor 1047 is a circuit that specifies, from a reception signal sequence for the reception transducers Rk of the reception aperture Rx, a reception signal corresponding to the delay of a reception transducer Rk as the reception signal corresponding to the reception transducer Rk, based on ultrasound reflected from an observation point Pij.

For each transmission event, the delay processor 1047 acquires information indicating positions of the reception transducers Rk from the reception aperture setter 1043, the reception signals for the reception transducers Rk from the data storage 107, the information indicating the position of the target region Bx from the target region setter 1042, and the delay to apply to the reception signal sequence of the reception transducers Rk from the delay calculator 1046. For each transmission event, from a reception signal sequence for the reception transducers Rk and using time of ultrasound transmission as a reference, the delay processor 1047 specifies a reception signal corresponding to a time after subtraction of the delay for a reception transducer Rk as a reception signal based on ultrasound reflected from an observation point Pij, and outputs to the summing unit 1049.

vii) Weight Calculator 1048

The weight calculator 1048 is a circuit that calculates a weight sequence (reception apodization) with respect to each reception transducer Rk such that a weight of a transducer positioned at a center of the reception aperture Rx in the array direction is a maximum weight.

As illustrated in FIG. 6, the weight sequence is a numerical sequence of weight coefficients that are to be applied to reception signals for the reception transducers in the reception aperture Rx. The weight sequence indicates weights that have a symmetrical distribution centered on a transducer xk that is spatially closest to the observation point Pij. As the shape of distribution of the weights indicated by the weight sequence, any shape is applicable, including but not limited to a Hamming window, a Hann window, and a rectangular window. The weight sequence is set so that the maximum weight is set with respect to the reception transducer located at the center position of the reception aperture Rx in the transducer array direction, and the central axis of the weight distribution coincides with the reception aperture central axis Rxo. The weight calculator 1048 receives an input of information indicating the positions of the reception transducers Rk, which is output from the reception aperture setter 1043, and calculates the weight sequence for the reception transducers Rk and outputs to the summing unit 1049. In the above structure, the weight sequence indicates weights distributed symmetrically with respect to the transducer xk, which is spatially closest to the observation point Pij. Alternatively, the transmission focal point F may coincide with the reception aperture central axis Rxo and the weight sequence may indicate weights distributed symmetrically with respect to the transmission focal point F.

viii) Summing Unit 1049

The summing unit 1049 is a circuit that accepts as input reception signals identified as corresponding to reception transducers Rk outputted from the delay processor 1047 and sums the reception signals to generate acoustic line signals subject to delay-and-sum processing with respect to observation points P. Alternatively, the summing unit 1049 may be configured to receive the weight sequence with respect to each reception transducer Rk outputted from the weight calculator 1048, multiply reception signals identified as corresponding to reception transducers Rk by weights corresponding to the reception transducers Rk, and generate acoustic line signals with respect to observation points Pij. The summing unit 1049 sums the reception signals for the reception transducers Rk after the reception signals have been aligned in phase by the delay processor 1047. Due to this, the summing unit 1049 is capable of increasing the S/N ratio of the reception signals received by the reception transducers Rk based on reflected ultrasound from the observation point Pij, and reception signals for the observation point Pij can be extracted.

As a result of one transmission event and processing accompanying the transmission event, acoustic line signals are generated for all observation points Pij in the target region Bx. By repeatedly performing transmission events while shifting the transmission aperture Tx in the transducer array direction by the movement pitch Mp each time, all of the transducer 101a of the probe 101 perform ultrasound transmission, a sub-frame acoustic line signal is generated for each transmission event, and sub-frame acoustic line signals for multiple transmission events are synthesized. As a result, a frame acoustic line signal is generated, which is a result of synthesizing acoustic line signals corresponding to one frame.

In the present disclosure, acoustic line signals synthesized for each observation point, making up a frame acoustic line signal, are each referred to as a synthesized acoustic line signal.

The summing unit 1049, for each transmission event, generates a sub-frame acoustic line signal for every observation point Pij in the target region Bx. The sub-frame acoustic line signals so generated are output to be stored in the data storage 107.

(5) Synthesizer 1140

Figure 8:
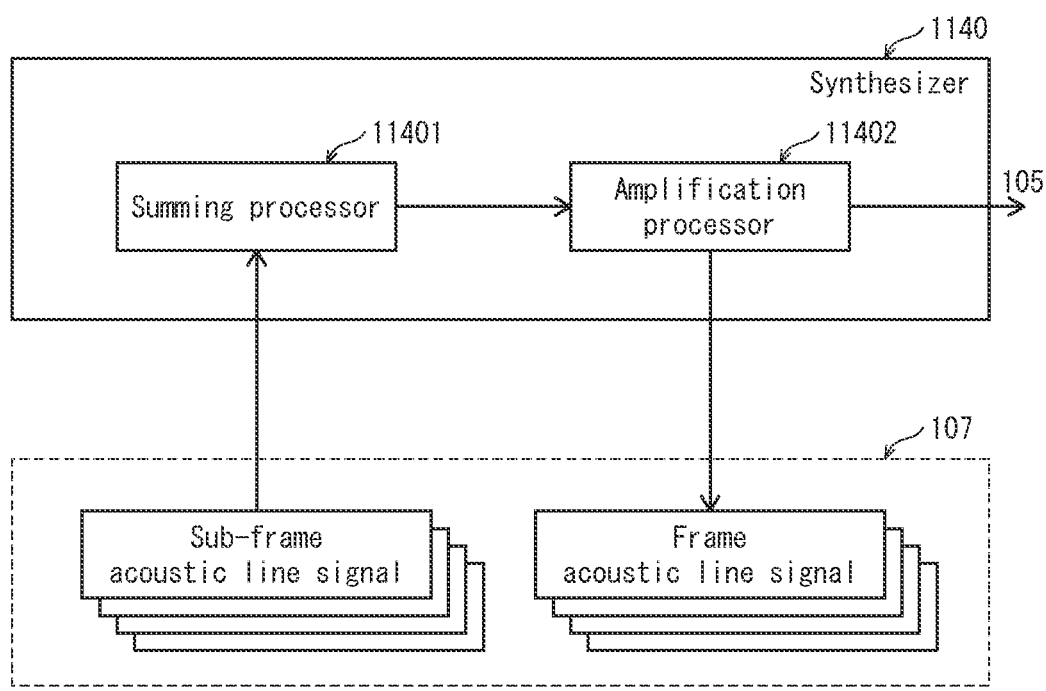
FIG. 8 is a function block diagram illustrating structure of a synthesizer 1140 pertaining to at least one embodiment.

The synthesizer 1140 is a circuit that synthesizes a frame acoustic line signal from sub-frame acoustic line signals generated for transmission events. FIG. 8 is a function block diagram illustrating the structure of the synthesizer 1140. As illustrated in FIG. 8, the synthesizer 1140 includes a summing processor 11401 and an amplification processor 11402.

The following describes the structure of each element of the synthesizer 1140.

i) Summing Processor 11401

The summing processor 11401, after the generation of a series of sub-frame acoustic line signals for synthesizing a frame acoustic line signal is completed, reads out the sub-frame acoustic line signals from the data storage 107. Further, using positions of observation points Pij for which acoustic line signals are acquired included in the sub-frame acoustic line signals as an index, the summing processor 11401 generates a synthesized acoustic line signal for each observation point Pij by summing the sub-frame acoustic line signals, thereby generating synthesized acoustic line signals corresponding to the observation points Pij to synthesize a frame acoustic line signal. Due to this, acoustic line signals for an observation point at a specific position that are included in different sub-frame acoustic line signals are summed to generate a synthesized acoustic line signal.

Figure 9:
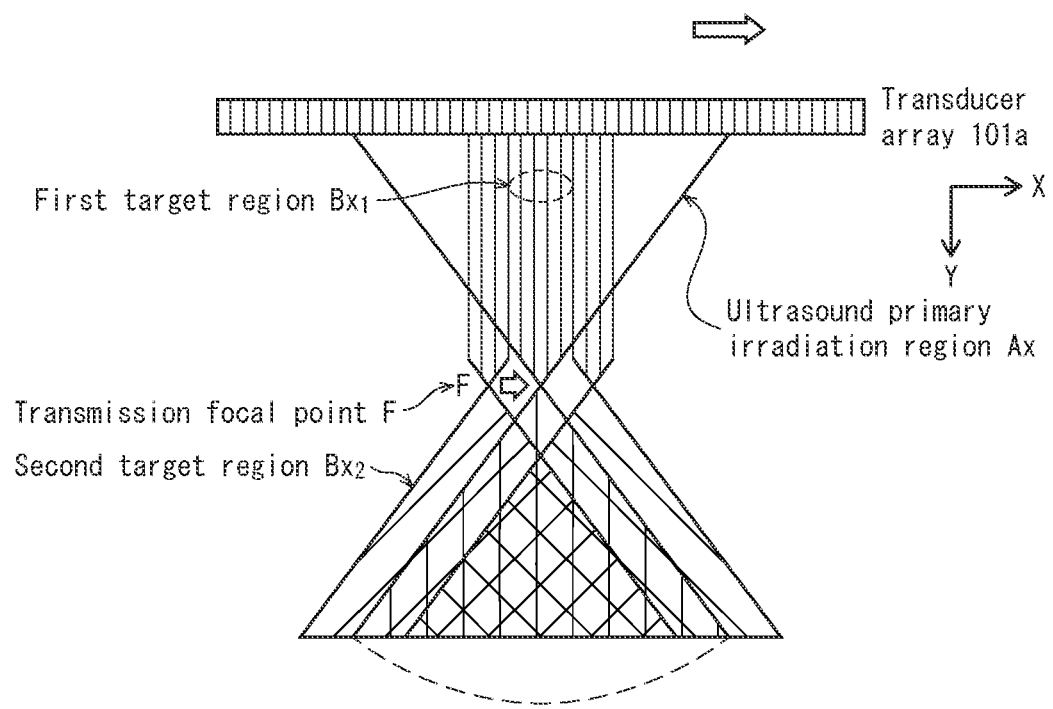
FIG. 9 is a schematic diagram illustrating synthesis processing for generating a synthesized acoustic line signal by a summing processor 11401 pertaining to at least one embodiment.

FIG. 9 is a schematic diagram illustrating processing by the summing processor 11401 for generating a synthesized acoustic line signal. As described above, ultrasound transmission is performed by repeatedly performing transmission events and shifting the transmission transducer array (transmission aperture Tx) in the transducer array direction by the movement pitch Mp (e.g. one transducer) each time. Thus, target regions Bx for two consecutive transmission events differ in position from one another in the transducer array direction by the width of the movement pitch Mp (e.g. one transducer). Thus, a frame acoustic line signal covering all target regions Bx can be generated by synthesizing sub-frame acoustic line signals based on the positions of the observation points Pij from which the acoustic line signals included in the sub-frame acoustic line signals are acquired. However, as described above, there is no overlap in the first target region Bx1 among transmission events, and therefore there are no observation points Pij common to multiple transmission events. That is, processing summing acoustic line signals is not performed for the first depth region, and is performed for the second depth region.

Further, for an observation point included in multiple target regions Bx, values of a plurality of acoustic line signals included in different sub-frame acoustic line signals are summed. Thus, the synthesized acoustic line signal for such an observation point may indicate a large value, depending upon the number of target regions Bx in which the observation point is included. In the following, the number of different target regions Bx in which a given observation point is included is referred to as an overlap count, and the maximum value of the overlap count in the transducer array direction is referred to as a maximum overlap count.

Further, according to the present embodiment, in the first depth region the target region Bx is a substantially rectangular region, and in the second depth region the target region Bx is a substantially triangular region. As illustrated in FIG. 10A, the overlap count varies in the depth direction of the subject. Accordingly, there is a depth-direction variance in values of synthesized acoustic line signals due to the influence of the overlap count varying in the depth direction. However, as described above, the first target region Bx1 is set such that there are no observation points Pij belonging to a plurality of transmission events, and therefore the overlap count is fixed at one regardless of depth in the first depth range. Accordingly, only in the second depth range, the overlap count increases to larger values as depth increases.

When summing is performed using positions of observation points Pij for which acoustic line signals included in sub-frame acoustic line signals are acquired as an index, the summing may be performed assigning weights to the positions of the observation points Pij.

A synthesized frame acoustic line signal is outputted to the amplification processor 11402.

ii) Amplification Processor 11402

As described above, there is a depth-direction variation in values of synthesized acoustic line signals due to the influence of the overlap count. In order to compensate for such variation in values of synthesized acoustic line signals, the amplification processor 11402, in synthesizing the synthesized acoustic line signals to generate the frame acoustic line signal, performs amplification of multiplying the synthesized acoustic line signals by amplification factors determined according to the number of acoustic line signals summed to yield the synthesized acoustic line signal (the overlap count).

Further, there is a depth-direction variation in values of acoustic line signals prior to synthesis due to attenuation of ultrasound. More specifically, as illustrated in FIG. 10B, values of acoustic line signals decay exponentially with depth. In order to compensate for the attenuation, the amplification processor 11402, performs gain control processing on synthesized acoustic line signals included in a frame acoustic line signal by multiplying each synthesized acoustic line signal by an amplification factor determined by depth.

The gain control processing is described in more detail below. As an amplification factor determined according to the number of times summing is performed (overlap count), 1/n, where n is the overlap count, can be adopted as the amplification factor, for example. Further, as an amplification factor determined according to the depth, $e^{ky}$, where k is a positive real number, can be used as the amplification factor with respect to a depth y, for example.

FIG. 10C is a schematic diagram illustrating an overview of the amplification performed by the amplification processor 11402. As described above, the overlap count increases as depth in the subject increases in the second depth range, and values of acoustic line signals decrease as depth in the subject increases. Accordingly, as indicated by an amplification factor Gc in FIG. 10C, the amplification factor increases with each increase in depth, and decreases with each increase in the overlap count. The amplification eliminates a variation factor of synthesized acoustic line signals due to variation of the overlap count and a variation factor of acoustic line signals due to ultrasound attenuation, such that values of synthesized acoustic line signals after the amplification can be made uniform in the depth direction.

Further, the synthesized acoustic line signals may be multiplied by amplification factors varying in the transducer array direction that are calculated based on overlap counts. This amplification eliminates a variation factor when there is variation in overlap counts in the transducer array direction, such that values of synthesized acoustic line signals after the amplification can be made uniform in the transducer array direction.

<Operations>

The following describes the operations of the ultrasound diagnostic device 100 as described above.

FIG. 11 is a flowchart illustrating frame acoustic line signal generation operations of the ultrasound diagnostic device 100.

First, in step S101, the transmitter 1031 performs transmission processing (a transmission event) of supplying a transmission signal causing transmission of an ultrasound beam to each transmission transducer of the transmission aperture Tx among the transducers 101a of the probe 101.

In step S102, the receiver 1040 generates reception signal sequences based on electric signals yielded through the reception of reflected ultrasound by the probe 101, and outputs the reception signal sequences to be stored in the data storage 107. Then, a determination is made of whether or not all the transducers 101a of the probe 101 have performed ultrasound transmission (step S103). When one or more of the transducers 101a have not yet performed ultrasound transmission, processing returns to step S101, which results in another transmission event being executed after shifting the transmission aperture Tx in the transducer array direction by the movement pitch Mp. When all of the transducers 101a have performed ultrasound transmission, processing proceeds to step S210.

In step S210, the target region setter 1042 sets a target region Bx based on information indicating the position of the transmission aperture Tx for the transmission event. In the initial loop of processing, the target region setter 1042 sets a target region Bx that can be calculated from the transmission aperture Tx for the initial transmission event.

Subsequently, processing proceeds to observation point synched beamforming (step S220 (including steps S221 through S228)). In step S220, first, coordinates i and j indicating a position of an observation point Pij of the target region Bx are initialized to minimum values (steps S221 and S222). Then, the reception aperture setter 1043 sets a reception aperture Rx so that the center of the reception aperture Rx corresponds to a transducer Xk that is spatially closest to the observation point Pij (step S223).

Subsequently, an acoustic line signal is generated for the observation point Pij (step S224).

Figure 12:
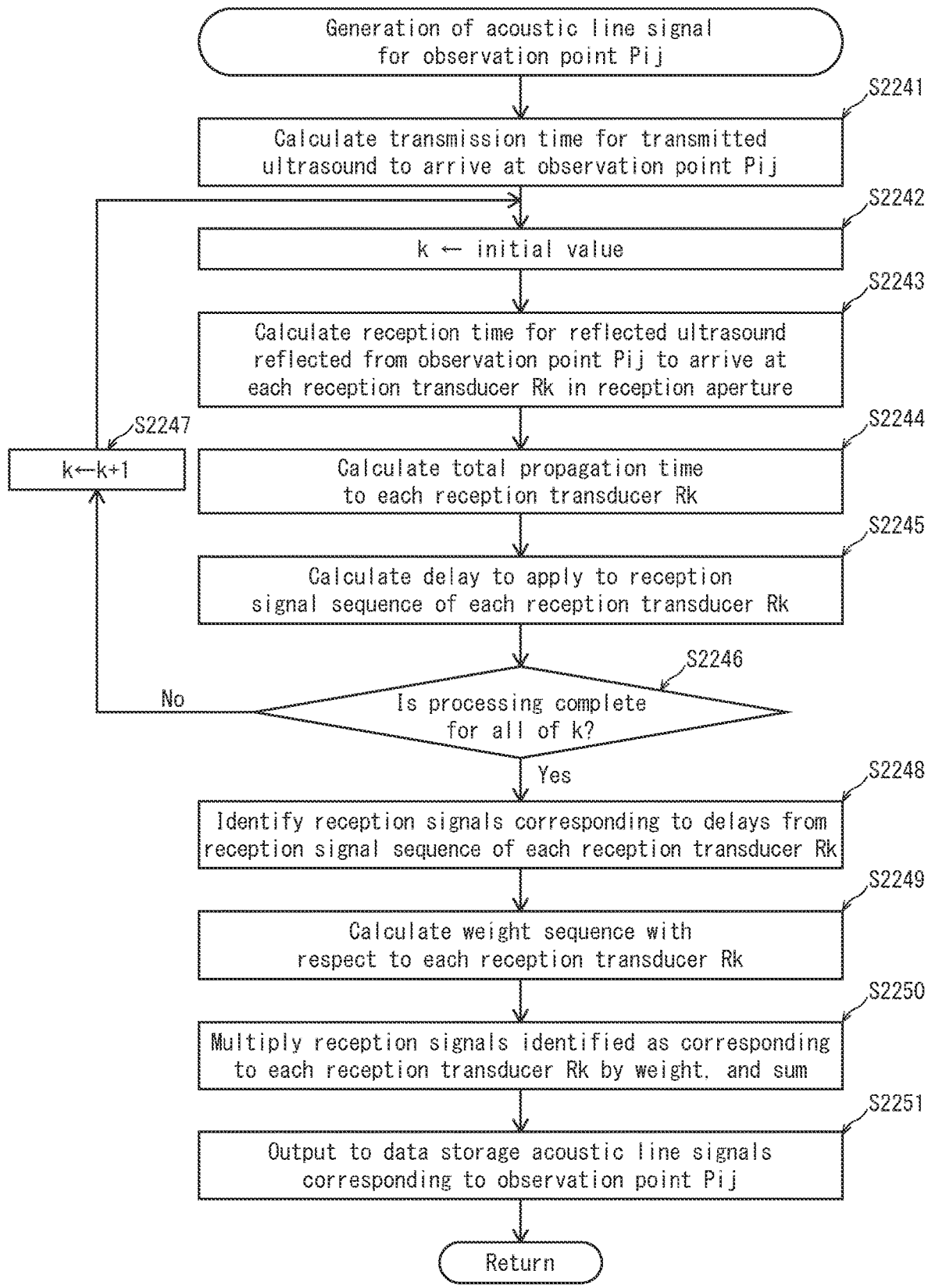
FIG. 12 is a flowchart illustrating acoustic line signal generation operations with respect to an observation point Pij, performed by the reception beamformer 104 pertaining to at least one embodiment.
Figure 13:
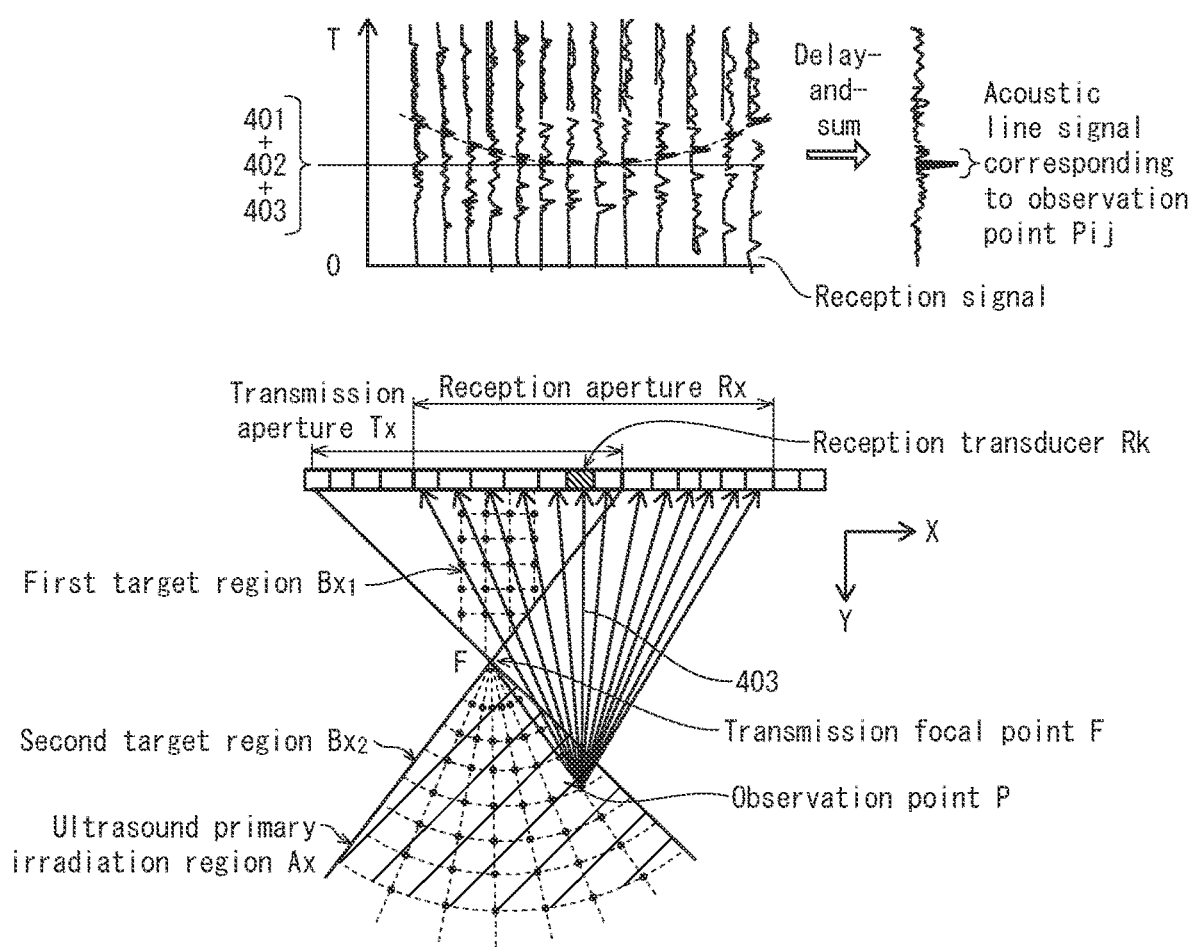
FIG. 13 is a schematic diagram for explaining the acoustic line signal generation operations with respect to an observation point Pij, performed by the reception beamformer 104 pertaining to at least one embodiment.

The following describes the operations in step S224 for generating an acoustic line signal for the observation point Pij. FIG. 12 is a flowchart illustrating acoustic line signal generation operations of the reception beamformer 104 for the observation point Pij. FIG. 13 is a schematic diagram for explaining the acoustic line signal generation operations of the reception beamformer 104 for the observation point Pij.

First, in step S2241, the transmission time calculator 1044 calculates, for any observation point Pij in the target region Bx, a transmission time required for transmitted ultrasound to arrive at the observation point Pij. The transmission time can be calculated by dividing the length of a geometrically determined path by the ultrasound speed cs. (1) When the observation point Pij is deeper than the focal depth, the length is that of the path (404+405) from a center of a transmission aperture Tx to the observation point Pij via the transmission focal point F. (2) When the observation point Pij is at or shallower than the focal depth, the length is either that of the path (402) from the center of the transmission aperture Tx to the observation point Pij or that of the path (401) from the center of the transmission aperture Tx to the reference point R on the transmission aperture central axis Txo that has the same y coordinate as the observation point Pij.

Subsequently, coordinate k, which indicates the position of a reception transducer Rk of the reception aperture Rx, is initialized to the minimum value in the reception aperture Rx (step S2242). Then, the reception time of time required for transmitted ultrasound to arrive at the reception transducer Rk after being reflected at the observation point Pij is calculated (step S2243). The reception time can be calculated by dividing the geometrically calculated length of the path 403 from the observation point Pij to the reception transducer Rk by the ultrasound speed cs. Further, from a sum of the transmission time and the reception time, the total propagation time required for ultrasound transmitted from the transmission aperture Tx to arrive at the reception transducer Rk after being reflected at the observation point Pij is calculated (step S2244). Further, based on the difference in total propagation times between different reception transducers Rk composing the reception aperture Rx, the delays for the reception transducers Rk are calculated (step S2245).

Subsequently, a determination is made of whether or not a delay has been calculated for every reception transducer Rk of the reception aperture Rx (step S2246). When a delay has not yet been calculated for one or more of the reception transducers Rk, the coordinate k is incremented (step S2247), and a delay for another reception transducer Rk is calculated (step S2243). When a delay has been calculated for every reception transducer Rk of the reception aperture Rx, processing proceeds to step S2248. At this point, a delay for ultrasound reflected from the observation point Pij has been calculated for each reception transducer Rk of the reception aperture Rx.

In step S2248, the delay processor 1047, for each reception transducer Rk, specifies a reception signal based on reflected ultrasound from the observation point Pij. Here, the delay processor 1047 specifies, from a reception signal sequence corresponding to each reception transducer Rk, a reception signal corresponding to a time after subtraction of the delay for the reception transducer Rk.

Subsequently, the weight calculator 1048 calculates a weight sequence for the reception transducers Rk of the reception aperture Rx, so that the maximum weight is set with respect to the reception transducer located at the center position of the reception aperture Rx in the transducer array direction (S2249). The summing unit 1049 generates an acoustic line signal for the observation point Pij by multiplying the specified reception signal for each reception transducer Rk by a weight corresponding to the reception transducer Rk and summing the weighted reception signals (step S2250). Following this, the summing unit 1049 outputs the acoustic line signal for the observation point Pij to the data storage 107 to be stored in the data storage 107 (step S2251).

Returning to FIG. 11, an acoustic line signal is generated for each observation point Pij (illustrated in FIG. 13 as black dots) of the target region Bx by repeating steps S223, S224 while incrementing the coordinates i and j. Subsequently, a determination is performed of whether an acoustic line signal has been generated for all observation points Pij of the target region Bx (steps S225, S227). When an acoustic line signal has not yet been generated for every observation point Pij of the target region Bx, the coordinates i and j are incremented (steps S226, S228), yielding an acoustic line signal for another observation point Pij (step S224). When an acoustic line signal is generated for every observation point Pij of the target region Bx, processing proceeds to step S230. At this point, a sub-frame acoustic line signal has been generated for each observation point Pij of the target region Bx for the transmission event, and the sub-frame acoustic line signals have been output to and stored in the data storage 107.

Subsequently, a determination is performed of whether or not a sub-frame acoustic line signal has been generated for every transmission event (step S230). When sub-frame acoustic line signals have not been generated for one or more transmission events, processing proceeds to step S210, where the coordinates i and j are initialized to minimum values in the target region Bx for the next transmission event, which can be calculated from the transmission aperture Tx for the next transmission event (steps S221 and S222), and then a reception aperture Rx is set (step S223) and generation of acoustic line signals is performed (step S224). When sub-frame acoustic line signals have been generated for every transmission event, processing proceeds to step S301.

In step S301, the summing processor 11401 reads out the sub-frame acoustic line signals stored in the data storage 107, and sums the sub-frame acoustic line signals using positions of the observation points Pij as an index. Thus, a synthesized acoustic line signal is generated for each observation point Pij to generate a frame acoustic line signal. Subsequently, the amplification processor 11402 multiplies each synthesized acoustic line signal by an amplification factor determined based on the number of acoustic line signals included in the sub-frame acoustic line signals (step S302). Further, the amplification processor 11402 outputs the amplified frame acoustic line signal to the ultrasound image generator 105 and the data storage 107 (Step S303), and processing ends.

<Effects of Embodiments>

The following describes differences between effects of conventional synthetic aperture methods and reception beamforming pertaining to the present disclosure.

Figure 14B:
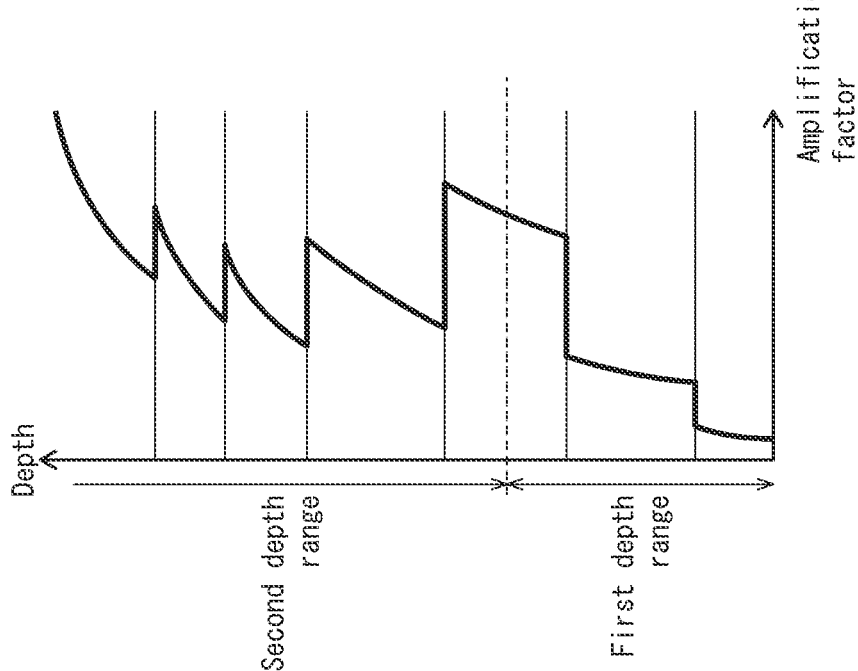
FIG. 14A and FIG. 14B are schematic diagrams pertaining to a reference example, illustrating an overview of overlap counts of synthesized acoustic line signals and amplification by the amplification processor 11402.
Figure 14A:
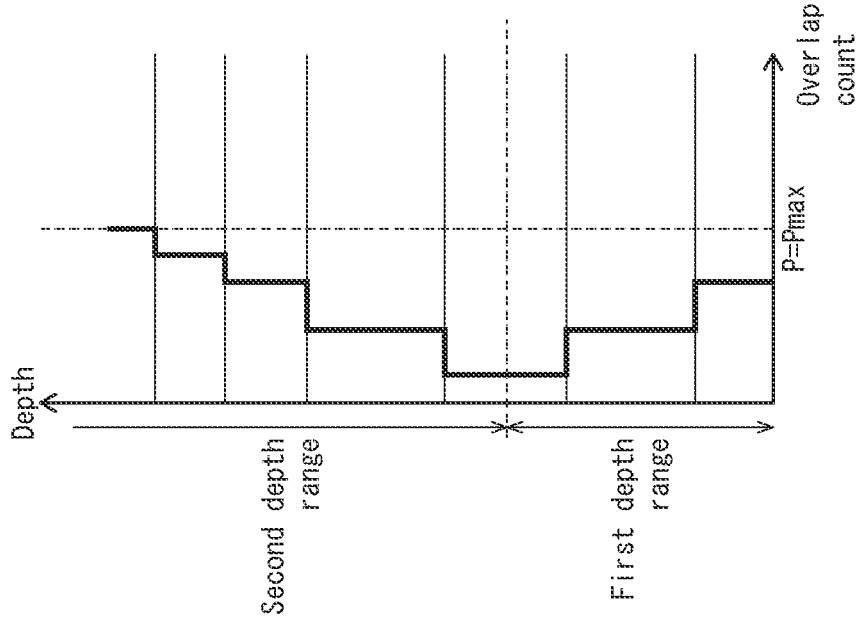

According to a reference example of a conventional synthetic aperture method, an entire area of the ultrasound primary irradiation region Ax illustrated in FIG. 2 is set as a target region. Thus, although in the second depth range the shape of the target region is the same as the second target region Bx2 of at least one embodiment, in the first depth range the width in the array direction is narrowest at the focal depth and becomes wider as it approaches the ultrasound probe. Accordingly, as illustrated in FIG. 14A, the overlap count is the same as that of at least one embodiment in the second depth range, but in the first depth range the overlap count has a profile symmetrical to the second depth range about the focal depth. That is, in the first depth range, the overlap count increases approaching the ultrasound probe. Accordingly, as illustrated in FIG. 14B, in order to eliminate both a variation factor in synthesized acoustic line signals of changes in overlap counts and a variation factor of acoustic line signals due to ultrasound attenuation, it is necessary to increase an amplification factor as depth increases and to multiply the synthesized acoustic line signals by an amplification factor that decreases each time the overlap count increases. In particular, in a shallowest portion near the ultrasound probe, acoustic line signal values are high and the overlap count is high, and therefore a small amplification factor is required. Thus, even if a large number of observation points Pij are provided in the shallowest portion near the ultrasound probe, the contribution to quality improvement of the frame acoustic line signal as a whole is small. Further, according to the reference example, in particular in the first depth range, the amplification factor changes greatly at depths where the overlap count changes. Accordingly, the amplification factor changes discontinuously at depth boundaries where the overlap count changes, and therefore values of a frame acoustic line signal tend to change discontinuously at the depth boundaries where the overlap count changes. That is, for example in a B mode image, a change in color tone may occur at a depth where the overlap count changes, leading to horizontal stripe noise.

In contrast, according to the reception beamforming pertaining to at least one embodiment, in the first depth range the first target region Bx1 is only in the vicinity of the transmission aperture central axis Txo in the ultrasound primary irradiation region Ax. Accordingly, the number of observation points in the first depth range is greatly reduced, and therefore the calculation load can be greatly reduced. Further, in the first depth range, the overlap count is fixed at one, and therefore discontinuous changes in the amplification factor caused by overlap count changes do not occur. Accordingly, discontinuous changes in values of frame acoustic line signals do not occur.

Further, as described above, according to the reference example, in the first depth range, the quality of the sub-fame acoustic line signals increases with proximity to the ultrasound probe, and therefore the quality of the frame acoustic line signal increases with proximity to the ultrasound probe, and therefore, in comparison, a user may be given a poor impression of quality of the frame acoustic line signal in the second depth range. In contrast, according to the reception beamforming pertaining to at least one embodiment, the overlap count is constant in the first depth range, and therefore uniformity of quality of the frame acoustic line signal is higher than that of a frame acoustic line signal obtained by using a conventional synthetic aperture method. Further, quality of the frame acoustic line signal is unlikely to be excessively high in the vicinity of the ultrasound probe, and therefore a difference in quality of the frame acoustic line signal between the first depth region and the second depth region can be kept small.

Further, in the first depth range, the overlap count is fixed at one, or in other words synthesis is not performed, and therefore even if there is movement in the subject, or relative movement between the subject and the ultrasound probe, reflected ultrasound from different positions in the subject will not be synthesized as a frame acoustic line signal with respect to one observation point, and reflected ultrasound from one observation point in different states will not be synthesized as a frame acoustic line signal. Accordingly, when there is movement in the subject or relative movement between the subject and the ultrasound probe, in comparison with the reference example it is less likely that in the first depth range a ghost image is generated and less likely that a decrease in frame acoustic line signal quality occurs, meaning that image quality can be improved and usability for the user can be improved.

<Review>

As described above, the ultrasound diagnostic device 100 pertaining to the present embodiment, according to the synthetic aperture method, synthesizes acoustic line signals that are generated from different transmission events for observation points P at the same positions in the second depth range, which is deeper than the focal depth. This achieves the effect of performing virtual transmission focusing even for observation points P at depths other than that of the transmission focal point F. This improves spatial resolution and S/N ratio.

Further, the ultrasound diagnostic device 100 sets, as a target region for which sub-frame acoustic line signals are to be generated, the second target region in the second depth range to be equivalent to the entirety of the ultrasound primary irradiation region in the second depth range. Accordingly, it is possible to improve the use efficiency of ultrasound and the effect of the synthetic aperture method of improving spatial resolution and S/N ratio can be maximally utilized. On the other hand, in the first depth range where depth is less than or equal to the focal depth, the first target region is set to be in the vicinity of central axis of the transmitted ultrasound. Thus, it becomes possible to reduce calculation load by reducing the number of observation points for the first depth region, where S/N ratio and spatial resolution of the frame acoustic line signal is sufficiently high without performing the synthetic aperture method. Further, because sub-frame acoustic line signal synthesis is not performed, the increase in S/N ratio and spatial resolution of a frame acoustic line signal nearer the ultrasound probe can be avoided, and therefore dependence of S/N ratio and spatial resolution of frame acoustic line signals on depth can be reduced to improve uniformity.

Further, according to the ultrasound diagnostic device 100, sub-frame acoustic line signal synthesis is not performed with respect to the first depth range, and therefore even if the subject moves or there is relative movement between the subject and the ultrasound probe, the movement is less likely to influence the frame acoustic line signal and convenience for the user can be increased.

Further, according to the ultrasound diagnostic device 100, the reception aperture setter 1043 selects, as transducers of the reception aperture Rx, transducers forming an array whose center position in the transducer array direction matches a transducer that is spatially closest to the observation point P. Accordingly, the ultrasound diagnostic device 100 performs reception beamforming by using a reception aperture that is not dependent upon transmission events but is dependent upon the position of the observation point P, and that is symmetric with respect to the observation point P. Due to this, the reception aperture Rx for a given observation point P is constant between different transmission events, between which the transmission focal point F is shifted in the transducer array direction. Thus, delay-and-sum processing for the same observation point P is always performed by using the same reception aperture Rx. In addition, a weight sequence is set so that the closer a reception transducer is to the observation point P, the greater the weight applied to the reception transducer. Due to this, even taking into account the fact that ultrasound attenuates as propagation distance increases, ultrasound reflected from the observation point P can be received with the highest sensitivity. Accordingly, the ultrasound diagnostic device 100 achieves high spatial resolution and S/N ratio.

According to the above embodiment, the reception aperture Rx for each observation point P is selected so that center position of the reception aperture Rx in the transducer array direction corresponds to a transducer that is spatially closest to the observation point P. Alternatively, the reception aperture Rx may be selected so that the center position of the reception aperture Rx corresponds to the focal point.

<<Modification 1>>

According to at least one embodiment, as indicated by an amplification factor Gc in FIG. 10C, the amplification processor 11402 increases the amplification factor as depth increases, and decreases the amplification factor with each increase in the overlap count, the amplification factor being used as a multiplier of synthesized acoustic line signals. The amplification eliminates a variation factor of synthesized acoustic line signals due to variation of the overlap count and a variation factor of acoustic line signals due to ultrasound attenuation, such that values of synthesized acoustic line signals after the amplification can be made uniform in the depth direction. However, discontinuous change in values of the frame acoustic line signal may be avoided even in the second depth range.

The amplification factor $G_A$ in FIG. 10C is the amplification factor of the amplification processor pertaining to Modification 1. The amplification factor $G_A$ is different from the amplification factor $G_C$ in that it continuously and monotonously increases with depth. That is, the amplification factor $G_A$ does not change discontinuously with respect to depth. Thus, a variation factor of synthesized acoustic line signals due to variation of the overlap count is more strongly eliminated, such that values of synthesized acoustic line signals after the amplification can be made uniform in the depth direction.

Further, in FIG. 10C, the amplification factor $G_A$ is set to be smaller than the amplification factor $G_C$ in the first depth range. As a result, differences between synthesized acoustic line signals after amplification in the first depth range and the second depth range become smaller, so that quality of the frame acoustic line signal in the second depth range becomes relatively high. Accordingly, in a B mode image, ultrasound image quality in the second depth range can be made relatively high.

The amplification factor of Modification 1 is not limited to the amplification factor $G_A$ illustrated in FIG. 10C, and may be any amplification as long as values of synthesized acoustic line signals after amplification are made uniform in the depth direction and change continuously in the depth direction.

<<Modification 2>>

According to the ultrasound diagnostic device 100 pertaining to at least one embodiment, the reception aperture setter 1043 selects the reception aperture Rx so that the center position of the reception aperture Rx in the transducer array direction corresponds to a transducer that is spatially closest to the corresponding observation point P. However, if the total propagation time calculation method and the delay control based on the total propagation time are kept the same, there is no need for the positional relationship between the reception aperture Rx and the observation point Pij to be the same, and appropriate modification may be made.

Modification 2 is different from the embodiments described above in that a transmission synched reception aperture setter (hereinafter also referred to as a Tx reception aperture setter) is provided that matches the array center of the transmission aperture Tx to the array center of the reception aperture Rx. Other than the Tx reception aperture setter, components are the same as those described with reference to the embodiments described above, and therefore description thereof is not repeated here.

Figure 15:
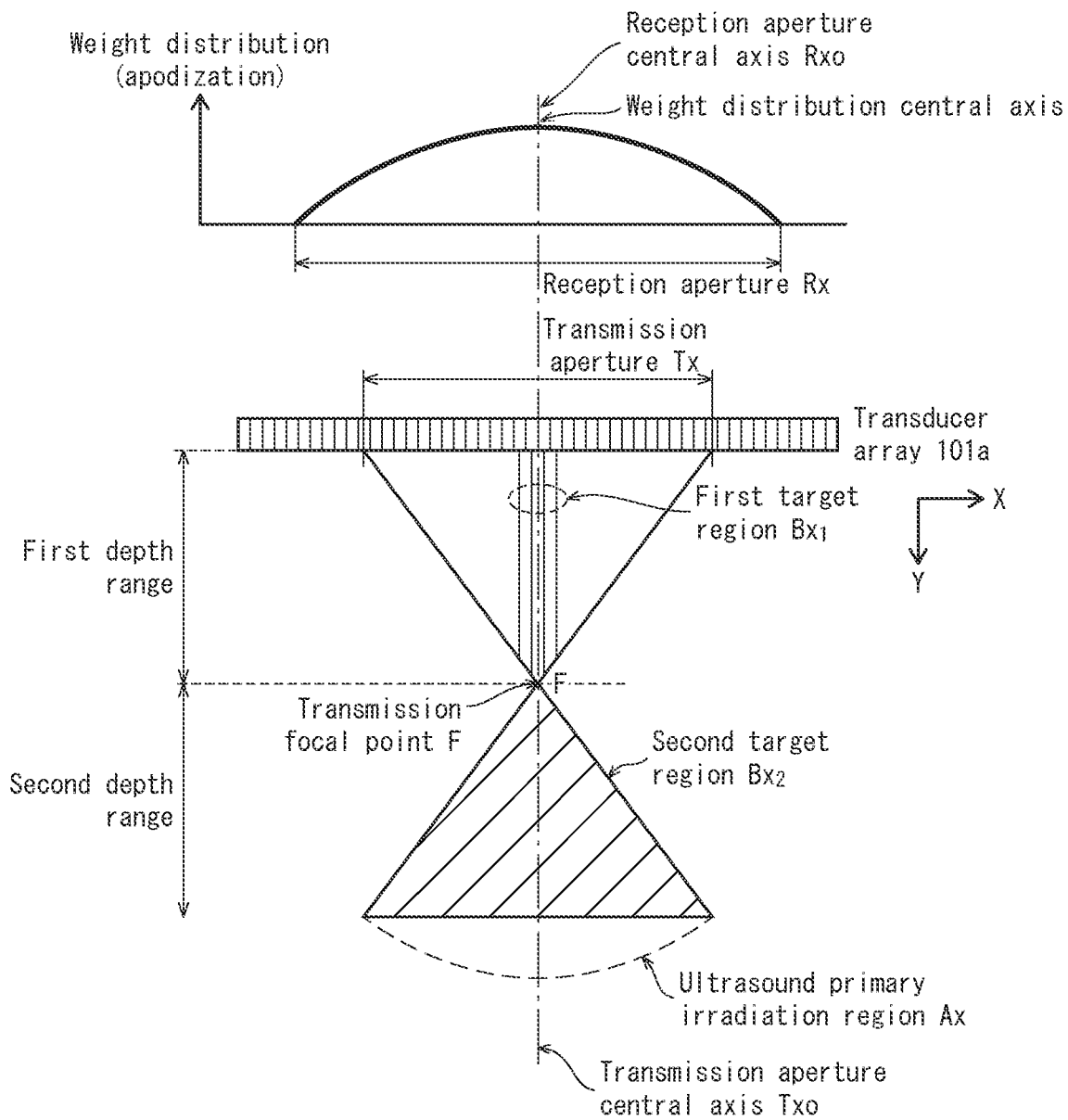
FIG. 15 is a schematic diagram illustrating a relationship between a transmission aperture Tx and a reception aperture Rx set by a reception aperture setter pertaining to Modification 2.

FIG. 15 is a schematic diagram illustrating a relationship between a reception aperture Rx and a transmission aperture Tx as set by the Tx reception aperture setter. According to Modification 2, the reception aperture Rx transducer array is selected so that the center position of the reception aperture Rx transducer array corresponds to the center position of the transmission aperture Tx transducer array. Thus, the position of the central axis Rxo of the reception aperture Rx is the same as the position of the central axis Txo of the transmission aperture Tx, and the reception aperture Rx is symmetric about the transmission focal point F. Accordingly, position of the reception aperture Rx also shifts in correspondence with position changes of the transmission aperture Tx shifting in the array direction per transmission event. On the other hand, with respect to one transmission event, the same reception aperture Rx is set for every observation point Pij in the target region Bx.

Further, a weight sequence (reception apodization) for the reception transducers Rk is calculated so that the maximum weight is set with respect to a transducer on the central axis Rxo of the reception aperture Rx and the central axis Txo of the transmission aperture Tx. The weight sequence indicates weights distributed symmetrically about a transducer Xi located on the central axis Rxo and the central axis Txo. As the shape of distribution of the weights indicated by the weight sequence, any shape is applicable, including but not limited to a Hamming window, a Hann window, and a rectangular window.

<Operations>

Figure 16:
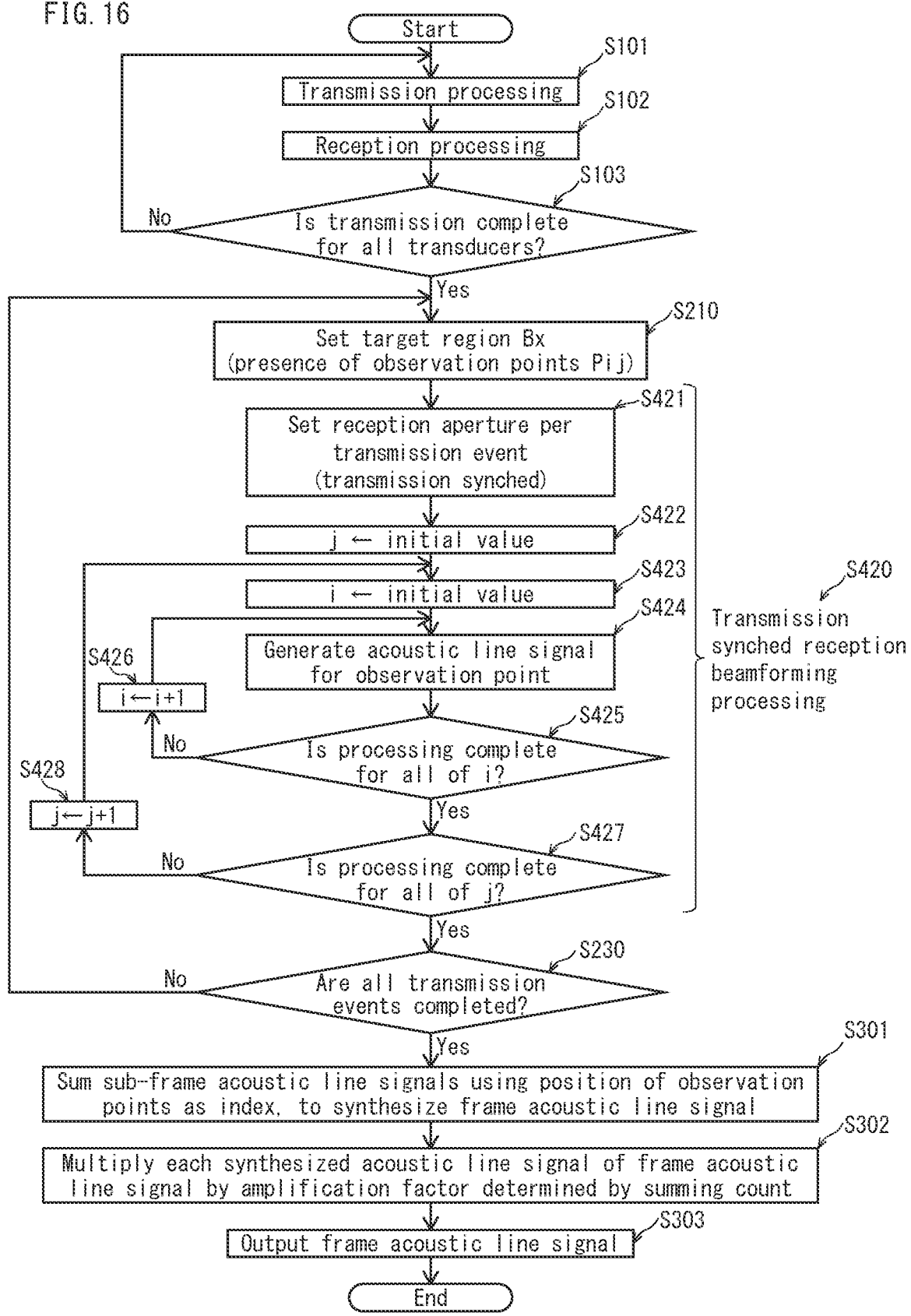
FIG. 16 is a flowchart illustrating frame acoustic line signal generation operations of an ultrasound diagnostic device pertaining to Modification 2.

FIG. 16 is a flowchart illustrating frame acoustic line signal generation by the ultrasound diagnostic device pertaining to Modification 2. The flowchart in FIG. 16 differs from the flowchart in FIG. 11 in that transmission synched beamforming (step S420 (including steps S421 through S428)) is performed in place of observation point synched beamforming (step S220 (including steps S221 through S228)). Meanwhile, the processing in steps other than step S420 are the same as in FIG. 11 and therefore description thereof is not repeated here.

In the processing of step S420, first, in step S421, the Tx reception aperture setter sets a reception aperture Rx for a transmission event by selecting reception transducers Rk composing a reception transducer array whose center position matches the center position of the transducer array composing the transmission aperture Tx for the corresponding transmission event.

Figure 17:
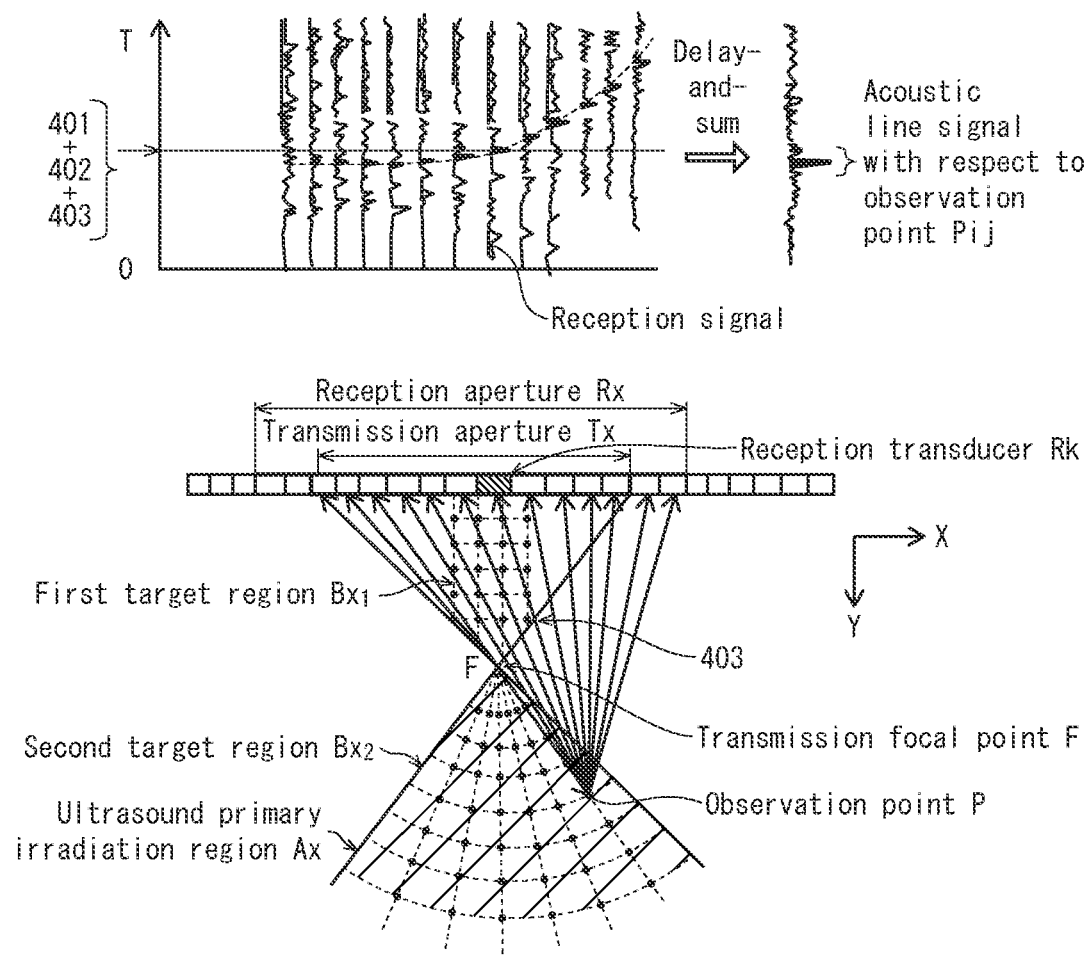
FIG. 17 is a schematic diagram for explaining acoustic line signal generation operations with respect to an observation point Pij, performed by a reception beamformer pertaining to Modification 2.

Subsequently, coordinates i and j indicating a position of an observation point Pij of the target region Bx are initialized to minimum values in the target region Bx set in step S210 (steps S422 and S423). Subsequently, an acoustic line signal is generated for the observation point Pij (step S424). FIG. 17 is a schematic diagram for explaining acoustic line signal generation operations with respect to an observation point Pij, performed by the reception beamformer pertaining to Modification 2. FIG. 17 differs from FIG. 13 in terms of the positional relationship between the transmission aperture Tx and the reception aperture Rx. The processing in step S424 is similar to that in step S224 of FIG. 11 (i.e., steps S2241 through S2251 in FIG. 12).

An acoustic line signal is generated for each observation point Pij (each illustrated in FIG. 17 as a black dot) of the target region Bx by repeating step S424 while incrementing the coordinates i and j. Subsequently, a determination is performed of whether an acoustic line signal has been generated for all of the observation points Pij of the target region Bx (steps S425, S427). When an acoustic line signal has not been generated for every observation point Pij of the target region Bx, the coordinates i and j are incremented (steps S426, S428), yielding an acoustic line signal for another observation point Pij (step S424). When an acoustic line signal has been generated for every observation point Pij of the target region Bx, processing proceeds to step S230. At this point, an acoustic line signal has been generated for each observation point Pij of the target region Bx for a transmission event, and the acoustic line signals are output to and stored in the data storage 107.

<Effects>

The ultrasound diagnostic device pertaining to Modification 2, described above, achieves the effects described as pertaining to the embodiments, excluding the effect related to setting an observation point synched reception aperture. In place of the effect related to setting an observation point synched reception aperture, the ultrasound diagnostic device pertaining to Modification 2 achieves the following effect. According to Modification 2, for each transmission event, the Tx reception aperture setter sets the reception aperture Rx by selecting reception transducers forming a transducer array whose center position corresponds to the center position of the transducer array composing the transmission aperture Tx for the transmission event. Thus, the position of the central axis Rxo of the reception aperture Rx is the same as the position of the central axis Txo of the transmission aperture Tx for the same transmission event and when transmission events are repeatedly performed, the transmission aperture Tx shifts in the transducer array direction each time, and the reception aperture Rx also shifts in the transducer array direction in synchronization with the transmission aperture Tx. Thus, a different reception aperture is used to perform delay-and-sum processing for each transmission event. Accordingly, although reception times are different, reception processing with respect to multiple transmission events can be performed by using a group of reception apertures covering a broad observation area. Thus, uniform spatial resolution is achieved over a broad observation area.

<<Other Modifications>>

(1) According to the embodiments and modifications described above, the second target region Bx2 covers the entire area of the ultrasound primary irradiation region Ax deeper than the focal depth. However, for example, the second target region Bx2 may be part of a portion of the ultrasound primary irradiation region Ax deeper than the focal depth, and as long as the second target regions Bx2 of consecutive transmission events overlap with each other, the shape and area of the second target region Bx2 are not limited to any one example. For example, methods such as narrowing width in the array direction of the second target region Bx2, decreasing density of observation points in the array direction relative to density of observation points in the depth direction, limiting a maximum width in the array direction of the second target region Bx2, and the like may be used to decrease the number of observation points.

(2) According to the embodiments and modifications described above, the first target region Bx1 is formed from four target lines in the vicinity of and parallel to the transmitted ultrasound central axis. However, as stated above, the number of target lines is not limited to four and may be any number. When the number of target lines is odd, frame acoustic line signal quality can be improved by matching one target line to the transmitted ultrasound central axis.

(3) According to the embodiments and modifications described above, the ultrasound probe is a linear probe. However, the ultrasound probe may be a convex probe. In this case, the first target region Bx1 may be formed from one or more target lines extending from a focal point of a convex probe surface, in the vicinity of the transmitted ultrasound central axis.

(4) The present disclosure is based on the embodiments above, but the present disclosure is not limited to these embodiments, and the following examples are also included in the scope of the present disclosure.

For example, the present disclosure may include a computer system including a microprocessor and a memory, the memory storing a computer program and the microprocessor operating according to the computer program. For example, the computer system may store a computer program of the ultrasound signal processing method, and the computer system may operate in accordance with the computer program or may provide instructions in accordance with the computer program to various components connected thereto.

Further, examples in which all or part of the ultrasound diagnostic device, or all or part of ultrasound signal processing device are constituted by a computer system including a microprocessor, a storage medium such as ROM, RAM, etc., a hard disk unit, and the like, are included in the present disclosure. In this implementation, a computer program achieving the same operations as a device described above is stored to the RAM or the hard disk unit. Further, in this implementation, various devices achieve their functions by the microprocessor operating in accordance with the computer program.

Further, all or part of the elements of each device may be configured as one system large scale integration (LSI). A system LSI is an ultra-multifunctional LSI manufactured by integrating multiple components onto one chip. Specifically, a system LSI is a computer system including a microprocessor, a ROM, a RAM, and the like. Further, each component may be separately implemented by using one chip, or some or all components may be implemented by using one chip. Here, LSI may refer to an integrated circuit, a system LSI, a super LSI, or an ultra LSI, depending on the level of integration. In this implementation, a computer program achieving the same operations as any device described above is stored to the RAM. Further, in this implementation, the system LSI achieves its functions by the microprocessor operating in accordance with the computer program. For example, a case in which the beamforming method of the present disclosure is stored as a program of an LSI, the LSI is inserted into a computer, and a defined program (beamforming method) is executed is also included in the present disclosure.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasonic diagnostic device pertaining to at least one embodiment may be implemented by execution of a program by a processor such as a CPU. All or part of the functions of an ultrasound diagnostic device pertaining to at least one embodiment may be implemented by a non-transitory computer-readable storage medium on which a program is stored that causes execution of a diagnostic method or beamforming method of an ultrasound diagnostic device described above. Further, execution of the program by another independent computer system may be achieved by transferring the program by recording the program or a signal onto a recording medium. The program may of course be distributed via means of transmission media such as the internet.

According to the ultrasound diagnostic device pertaining to at least one embodiment, the ultrasound diagnostic device includes a data storage, which is a storage device. However, the storage device is not limited to this example and a semiconductor memory, hard disk drive, optical disk drive, magnetic storage device, or the like may be externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, some of the steps of processing described above may be executed simultaneously (in parallel).

Further, the ultrasound diagnostic device is described as having an externally connected probe and display, but may be configured with an integral probe and/or display.

According to at least one embodiment, a probe configuration is illustrated in which the transducers are arranged along a one-dimensional direction. However, configuration of the probe is not limited to this. For example, a two-dimensional transducer array in which the transducers are arrayed on a two-dimensional plane or a rocking-type probe that acquires a three-dimensional tomographic image by mechanical rocking of a plurality of transducers arranged along a one-dimensional direction may be used as appropriate, depending on measurement requirements. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, a portion of functions of transmitters and receivers may be included in the probe. For example, a transmission electrical signal may be generated and converted to ultrasound in the probe, based on a control signal for generating a transmission electrical signal outputted from the transmitter. It is possible to use a structure that converts received reflected ultrasound into a reception electrical signal and generates a reception signal based on the reception electrical signal in the probe.

Further, at least a portion of functions of each ultrasound diagnostic device pertaining to an embodiment, and each modification thereof, may be combined. Further, the values used above are all illustrative, for the purpose of explaining the present disclosure in detail, and the present disclosure is not limited to the example values used above.

Further, the present disclosure includes various modifications that a person skilled in the art would arrive at based on the embodiment describe above.

<<Review>>

(1) The ultrasound signal processing device pertaining to an embodiment of the present disclosure is an ultrasound signal processing device comprising ultrasound signal processing circuitry, the ultrasound signal processing circuitry comprising: a transmitter that repeatedly performs a transmission event, changing a position of a transmission transducer array for each transmission event, the transmission event including selecting the transmission transducer array from transducers arrayed on an ultrasound probe and outputting a drive signal to the ultrasound probe for driving the transmission transducer array such that the transducers thereof transmit focused transmitted ultrasound; a receiver that receives signals from the ultrasound probe to generate reception signal sequences, the signals being based on reflected ultrasound reflected in a subject and acquired by the ultrasound probe for each transmission event; an observation point setter that, for each transmission event, sets observation points corresponding to positions in the subject; and a frame generator that generates a frame acoustic line signal based on the reception signal sequences corresponding to each of the observation points set by the observation point setter, wherein the observation point setter sets the observation points such that observation points in a first region each correspond to only one transmission event and observation points in a second region each correspond to more than one transmission event, where a focal region is where the transmitted ultrasound is most focused, the first region is closer than the focal region to the ultrasound probe, and the second region is farther than the focal region from the ultrasound probe.

Further, the ultrasound signal processing method pertaining to an embodiment of the present disclosure is an ultrasound signal processing method comprising: repeatedly performing a transmission event, changing a position of a transmission transducer array for each transmission event, the transmission event including selecting the transmission transducer array from transducers arrayed on an ultrasound probe and outputting a drive signal to the ultrasound probe for driving the transmission transducer array such that the transducers thereof transmit focused transmitted ultrasound; receiving signals from the ultrasound probe to generate reception signal sequences, the signals being based on reflected ultrasound reflected in a subject and acquired by the ultrasound probe for each transmission event; setting, for each transmission event, observation points corresponding to positions in the subject; and generating a frame acoustic line signal based on the reception signal sequences corresponding to each of the observation points set, wherein the observation points are set such that observation points in a first region each correspond to only one transmission event and observation points in a second region each correspond to more than one transmission event, where a focal region is where the transmitted ultrasound is most focused, the first region is closer than the focal region to the ultrasound probe, and the second region is farther than the focal region from the ultrasound probe.

According to the above structure and method, when using the synthetic aperture method, the computation load can be reduced and uniformity of acoustic line signal quality can be increased.

(2) According to at least one embodiment, the ultrasound signal processing device of (1), above, is configured such that the observation point setter sets observation points in the first region to be near a transmitted ultrasound central axis that is a straight line linking a center of the transmission transducer array to a center of the focal region.

According to the above structure, acoustic line signal quality can be increased in a region shallower than the focal region.

(3) According to at least one embodiment, the ultrasound signal processing device of (2), above, is configured such that the observation point setter sets observation points in the first region to be on the transmitted ultrasound central axis.

According to the above structure, frame acoustic line signals can also be generated in the region shallower than the focal region, from a region including a region where acoustic line signal quality is highest.

(4) According to at least one embodiment, the ultrasound signal processing device of any one of (1) to (3), above, is configured such that width in an array direction of the transmission transducer array of a target region in which observation points are set in the first region is equal to or less than a movement pitch in the array direction determined by a change in the position of the transmission transducer array per transmission event.

According to this structure, in the region shallower than the focal region, a target region in which each observation point corresponds to one transmission event can easily be set.

(5) According to at least one embodiment, the ultrasound signal processing device of (3) or (4), above, is configured such that the observation point setter sets all of the observation points in the first region to be on the transmitted ultrasound central axis.

According to the above structure, in the region shallower than the focal region, frame acoustic line signals can be generated from only a region where frame acoustic line signal quality is highest, and therefore a synthetic aperture method is not used and frame acoustic line signal quality can be uniformly and maximally improved in the array direction of the transducer array.

(6) According to at least one embodiment, the ultrasound signal processing device of any one of (1) to (5), above, is configured such that the frame generator generates the frame acoustic line signal by using a synthetic aperture method with respect to the observation points in the second region.

According to the above structure, in a region deeper than the focal region, ultrasound use efficiency can be improved by the synthetic aperture method, and frame acoustic line signal quality can be improved by virtual transmission beamforming.

According to at least one embodiment, the ultrasound signal processing device of any one of (1) to (6), above, is configured such that the observation point setter sets a portion of an hourglass-shaped region that is farther than the focal region from the ultrasound probe as the second region, where the transmission transducer array is a base of the hourglass-shaped region and the focal region is the narrowest part of the hourglass-shaped region.

According to the above structure, ultrasound use efficiency can be maximized and acoustic line signal quality can be increased in a region deeper than the focal region.

(8) According to at least one embodiment, the ultrasound signal processing device of any one of (1) to (7), above, is configured such that the frame generator generates the frame acoustic line signal pertaining to the observation points from the reception signal sequences, based on transmission times and reception times, where the transmission times with respect to the observation points in the second region are the total times required for the transmitted ultrasound to propagate to each of the observation points in the second region, each of the transmission times being the sum of a time required for the transmitted ultrasound to propagate to a reference point in the focal region and a time required for the transmitted ultrasound to propagate from the reference point to one of the observation points, and each of the reception times being a time required for reflected ultrasound to propagate to a transducer of the ultrasound probe from one of the observation points.

According to the above structure, in a region deeper than the focal region, transmission beamforming can be performed with the transmission focal point as a virtual sound source.

(9) According to at least one embodiment, the ultrasound signal processing device of any one of (1) to (8), above, is configured such that the frame generator generates the frame acoustic line signal pertaining to the observation points from the reception signal sequences, based on transmission times and reception times, where the transmission times with respect to the observation points in the first region are each a time required for the transmitted ultrasound to propagate to one of the observation points, and each of the reception times is a time required for reflected ultrasound to propagate to a transducer of the ultrasound probe from one of the observation points.

According to the above structure, in the region shallower than the focal region, transmission time calculation can be simplified and calculation load can be decreased.

(10) According to at least one embodiment, the ultrasound signal processing device of any one of (1) to (9), above, is configured such that the frame generator further comprises a signal amplifier that corrects differences in signal strengths caused by differences in transmission event counts between observation points, the signal amplifier setting amplification factors with respect to the signal strengths, such that the amplification factors change continuously with distance between the ultrasound probe and the observation points.

According to the above structure, the amplification factor changes continuously between two spatially adjacent observation points, and therefore discontinuous change in values of frame acoustic line signals with respect to changes in distance between observation points and the ultrasound probe is suppressed, and generation of noise in the array direction can be suppressed.

(11) An ultrasound diagnostic device pertaining to at least one embodiment comprises an ultrasound probe and the ultrasound signal processing device of any one of (1) to (10), above.

Although one or more embodiments of the present disclosure have been described and illustrated in detail, the disclosed embodiments are made for the purposes of illustration and example only and not limitation. The scope of the present disclosure should be interpreted by the terms of the appended claims

What is claimed is:

1. An ultrasound signal processing device comprising ultrasound signal processing circuitry, the ultrasound signal processing circuitry comprising:
   a transmitter that repeatedly performs a transmission event while changing a position of a transmission transducer array for each of the transmission events, the transmission event including selecting the transmission transducer array from transducers on an ultrasound probe and outputting a drive signal to the ultrasound probe for driving the transmission transducer array such that the transducers thereof transmit focused transmitted ultrasound;
   a receiver that receives signals from the ultrasound probe to generate reception signal sequences, the signals from the ultrasound probe being based on reflected ultrasound, wherein the reflected ultrasound is ultrasound that is reflected in a subject and acquired by the ultrasound probe for each of the transmission events;
   a target region setter that, for each of the transmission events, sets a target region with observation points corresponding to positions in the subject; and
   a synthesizer that generates a frame acoustic line signal based on the reception signal sequences corresponding to each of the observation points in the target region set by the target region setter, wherein
   the target region setter sets the target region such that observation points in a first region of the target region each correspond to only one transmission event and observation points in a second region of the target region each correspond to more than one transmission event, where a focal region is where the transmitted ultrasound is most focused, the first region is in a first depth range that extends from the focal region to the ultrasound probe, and the second region is in a second depth range that is farther than the focal region from the ultrasound probe,
   the transmitter changes the position of the transmission transducer array for each of the transmission events by a movement pitch in an array direction,
   the first region is set as a substantially rectangular area in a vicinity of a central axis of the focused transmitted ultrasound, and
   a width of the first region throughout an entire length of the first depth range in a depth direction of the ultrasound probe is less than or equal to the movement pitch, whereby the first region of one of the transmission events does not overlap with the first region of another of the transmission events.

2. The ultrasound signal processing device of claim 1, wherein
   the target region setter sets the observation points in the first region to be near a transmitted ultrasound central axis that is a straight line linking a center of the transmission transducer array to a center of the focal region.

3. The ultrasound signal processing device to claim 2, wherein
   the target region setter sets the observation points in the first region to be on the transmitted ultrasound central axis.

4. The ultrasound signal processing device of claim 1, wherein
   the synthesizer generates the frame acoustic line signal by using a synthetic aperture method with respect to the observation points in the second region and without synthesis of acoustic line signals with respect to the observation points in the first region.

5. The ultrasound signal processing device of claim 1, wherein
the target region setter sets a portion of an hourglass-shaped region that is farther than the focal region from the ultrasound probe as the second region, where the transmission transducer array is a base of the hourglass-shaped region and the focal region is the narrowest part of the hourglass-shaped region.

6. The ultrasound signal processing device of claim 1, wherein
the synthesizer generates the frame acoustic line signal pertaining to the observation points in the target region from the reception signal sequences, based on transmission times and reception times, where the transmission times with respect to the observation points in the second region are total times required for the transmitted ultrasound to propagate to each of the observation points in the second region, each of the transmission times being a sum of a time required for the transmitted ultrasound to propagate to a reference point in the focal region and a time required for the transmitted ultrasound to propagate from the reference point to one of the observation points in the target region, and each of the reception times being a time required for reflected ultrasound to propagate to a transducer of the ultrasound probe from one of the observation points in the target region.

7. The ultrasound signal processing device of claim 1, wherein
the synthesizer generates the frame acoustic line signal pertaining to the observation points from the reception signal sequences, based on transmission times and reception times, where the transmission times with respect to the observation points in the first region are each a time required for the transmitted ultrasound to propagate to one of the observation points, and each of the reception times is a time required for reflected ultrasound to propagate to a transducer of the ultrasound probe from one of the observation points.

8. The ultrasound signal processing device of claim 1, wherein
the synthesizer further comprises a signal amplifier that corrects differences in signal strengths caused by differences in transmission event counts between observation points, and
the signal amplifier sets amplification factors with respect to the signal strengths, such that the amplification factors change continuously with distance between the ultrasound probe and the observation points.

9. The ultrasound signal processing device of claim 1, wherein
the target region setter is a delay-and-sum unit that, for each of the transmission events, sets the observation points by setting a target region and performs delay-and-sum processing for observation points in the target region and generates a sub-frame acoustic line signal, and
the synthesizer generates the frame acoustic line signal based on the reception signal sequences corresponding to the sub-frame acoustic line signals.

10. The ultrasound signal processing device of claim 1, wherein
the target region setter sets the observation points for the each of the transmission events by setting a target region, and the first region includes an entire portion of the target region that is closer than the focal region to the ultrasound probe and the second region includes an entire portion of the target region that is farther than the focal region from the ultrasound probe.

11. An ultrasound diagnostic device comprising:
an ultrasound probe; and
an ultrasound signal processing device comprising ultrasound signal processing circuitry, the ultrasound signal processing circuitry comprising:
a transmitter that repeatedly performs a transmission event while changing a position of a transmission transducer array for each of the transmission events, the transmission event including selecting the transmission transducer array from transducers on the ultrasound probe and outputting a drive signal to the ultrasound probe for driving the transmission transducer array such that the transducers thereof transmit focused transmitted ultrasound;
a receiver that receives signals from the ultrasound probe to generate reception signal sequences, the signals from the ultrasound probe being based on reflected ultrasound, wherein the reflected ultrasound is ultrasound that is reflected in a subject and acquired by the ultrasound probe for each of the transmission events;
a target region setter that, for each of the transmission events, sets a target region with observation points corresponding to positions in the subject; and
a synthesizer that generates a frame acoustic line signal based on the reception signal sequences corresponding to each of the observation points in the target region set by the target region setter, wherein
the target region setter sets the observation points such that observation points in a first region of the target region each correspond to only one transmission event and observation points in a second region of the target region each correspond to more than one transmission event, where a focal region is where the transmitted ultrasound is most focused, the first region is in a first depth range that extends from the focal region to the ultrasound probe, and the second region is in a second depth range that is farther than the focal region from the ultrasound probe,
the transmitter changes the position of the transmission transducer array for each of the transmission events by a movement pitch in an array direction,
the first region is set as a substantially rectangular area in a vicinity of a central axis of the focused transmitted ultrasound, and
a width of the first region throughout an entire length of the first depth range in a depth direction of the ultrasound probe is less than or equal to the movement pitch, whereby the first region of one of the transmission events does not overlap with the first region of another of the transmission events.

12. An ultrasound signal processing method comprising:
repeatedly performing a transmission event while changing a position of a transmission transducer array for each of the transmission events, the transmission event including selecting the transmission transducer array from transducers on an ultrasound probe and outputting a drive signal to the ultrasound probe for driving the transmission transducer array such that the transducers thereof transmit focused transmitted ultrasound; receiving signals from the ultrasound probe to generate reception signal sequences, the signals from the ultrasound probe being based on reflected ultrasound, wherein the reflected ultrasound is ultrasound that is reflected in a subject and acquired by the ultrasound probe for each of the transmission events;

setting, for each of the transmission events, a target region with observation points corresponding to positions in the subject; and generating a frame acoustic line signal based on the reception signal sequences corresponding to each of the observation points in the target region set, wherein the observation points are set such that observation points in a first region of the target region each correspond to only one transmission event and observation points in a second region of the target region each correspond to more than one transmission event, where a focal region is where the transmitted ultrasound is most focused, the first region is in a first depth range that extends from the focal region to the ultrasound probe, and the second region is in a second depth range that is farther than the focal region from the ultrasound probe, the position of the transmission transducer array changes for the each of the transmission events by a movement pitch in an array direction, the first region is set as a substantially rectangular area in a vicinity of a central axis of the focused transmitted ultrasound, and a width of the first region throughout an entire length of the first depth range in a depth direction of the ultrasound probe is less than or equal to the movement pitch, whereby the first region of one of the transmission events does not overlap with the first region of another of the transmission events.

* * * * *